US012331230B2

(12) United States Patent
Liu et al.

(10) Patent No.: US 12,331,230 B2
(45) Date of Patent: Jun. 17, 2025

(54) PROTEIN-BASED ADHESIVE AND ITS MODIFICATION

(71) Applicant: Purdue Research Foundation, West Lafayette, IN (US)

(72) Inventors: Julie C. Liu, West Lafayette, IN (US); Sydney E. Hollingshead, Cleveland, OH (US); Charng-Yu Lin, West Lafayette, IN (US); Jonathan J. Wilker, West Lafayette, IN (US)

(73) Assignee: Purdue Research Foundation

( * ) Notice: Subject to any disclaimer, the term of this patent is extended or adjusted under 35 U.S.C. 154(b) by 1040 days.

(21) Appl. No.: 17/270,095

(22) PCT Filed: Aug. 22, 2019

(86) PCT No.: PCT/US2019/047639
§ 371 (c)(1),
(2) Date: Feb. 22, 2021

(87) PCT Pub. No.: WO2020/041557
PCT Pub. Date: Feb. 27, 2020

(65) Prior Publication Data
US 2021/0207013 A1 Jul. 8, 2021

Related U.S. Application Data

(60) Provisional application No. 62/721,112, filed on Aug. 22, 2018.

(51) Int. Cl.
*C09J 189/00* (2006.01)
*A61L 24/10* (2006.01)
*C07K 14/78* (2006.01)
*C09J 11/04* (2006.01)

(52) U.S. Cl.
CPC ........... *C09J 189/00* (2013.01); *A61L 24/108* (2013.01); *C07K 14/78* (2013.01); *C09J 11/04* (2013.01)

(58) Field of Classification Search
CPC ........ C09J 189/00; C09J 11/04; A61L 24/108; C07K 14/78
See application file for complete search history.

(56) References Cited

U.S. PATENT DOCUMENTS

| 4,585,585 | A | 4/1986 | Waite | |
|---|---|---|---|---|
| 5,197,973 | A | 3/1993 | Pang et al. | |
| 6,506,577 | B1 * | 1/2003 | Deming | C07K 14/001 530/211 |
| 10,351,743 | B2 * | 7/2019 | Liu | C09J 189/00 |
| 2010/0003329 | A1 | 1/2010 | Elisseeff | |
| 2016/0346424 | A1 | 12/2016 | Lee et al. | |
| 2017/0015885 | A1 * | 1/2017 | Liu | C07K 7/06 |

FOREIGN PATENT DOCUMENTS

WO WO-2014027042 A2 * 2/2014 ............... A61F 2/02

OTHER PUBLICATIONS

Macewan, S.R. and Chilkoti, A., (2010). Elastin-like polypeptides: Biomedical applications of tunable biopolymers. Peptide Science: Original Research on Biomolecules, 94(1), pp. 60-77. DOI: doi.org/10.1002/bip.21327 (Year: 2010).*
Wang, Q., Xia, X., Huang, W., Lin, Y., Xu, Q. and Kaplan, D.L. (2014), High Throughput Screening of Dynamic Silk-Elastin-Like Protein Biomaterials. Adv. Funct. Mater., 24: 4303-4310. DOI: doi.org/10.1002/adfm.201304106 (Year: 2014).*
Xu et al. 2012. "Rheological properties of cysteine-containing elastin-like polypeptide solutions and hydrogels." Biomacromolecules 13.8 (2012): pp. 2315-2321 (Year: 2012).*
McMillan and Conticello. 2000. "Synthesis and characterization of elastin-mimetic protein gels derived from a well-defined polypeptide precursor". Macromolecules, 33(13), pp. 4809-4821. (Year: 2000).*
Muiznieks, L., "Genipin cross-linking of elastin and elastin-based proteins." Protein Scaffolds: Design, Synthesis, and Applications (2018): Chapter 17, pp. 213-221 (first available online Jun. 5, 2018) (Year: 2018).*
Brennan et al. 2018. "Critical factors for the bulk adhesion of engineered elastomeric proteins". R. Soc. open sci. 5: 171225. http://dx.doi.org/10.1098/rsos.171225, on the IDS filed Nov. 10, 2023 (Year: 2018).*
Brennan, M.J. et al., "A Bioinspired Elastin-Based Protein for a Cytocompatible Underwater Adhesive," Biomaterials, 124 (2017), pp. 116-125.
Brennan, M.J. et al., "Critical Factors for the Bulk Adhesion of Engineered Elastomeric Proteins," R. Soc. open sci. 5 (2018), pp. 1-14.
Hollingshead, S. et al., "Effect of Cross-Linkers on Mussel- and Elastin-Inspired Adhesives on Physiological Substrates," ACS Appl. Bio Mater. (2022), pp. 630-641).

(Continued)

*Primary Examiner* — Terry A McKelvey
*Assistant Examiner* — Andrew T Moehlman
(74) *Attorney, Agent, or Firm* — Purdue Research Foundation

(57) ABSTRACT

This invention relates to protein-based adhesives that are capable to adhere to a substrate in a dry, wet, moist, or an aqueous environment. Particularly, said adhesives comprise a crosslinking agent and an elastin-like polypeptide (ELP) that contain tyrosine, lysine, cysteine, dihydroxyphenylalanine (DOPA) or trihydroxyphenylalanine (TOPA) amino acid residue, or a combination thereof, on the polypeptide chain of said ELP. Among others, the adhesives disclosed herein may find broad applications in medical treatments and surgical operations. Compositions and methods of use are within the scope of this application.

4 Claims, 12 Drawing Sheets
Specification includes a Sequence Listing.

(56) References Cited

OTHER PUBLICATIONS

Hollingshead S. et al., "pH-Sensitive Mechanical Properties of Elastin-Based Hydrogels," Macromol. Biosci. (2020), pp. 1-12.
Lin, C-Y. et al., "Comparison between Catechol- and Thiol-Based Adhesion Using Elastin-like Polypeptides," ACS Appl. Bio Matear. 3, (2020), pp. 3894-3905.
Lin, C-Y, et al., "Incorporation of Short, Charged Peptide Tags Affects the Temperature Responsiveness of Positively-Charged Elastin-Like Polypeptides," J. Mater. Chem. B (2019), pp. 5245-5256.
Numata, K. et al., "Synthesis of Adhesive Peptides Similar to Those Found in Blue Mussel (*Mytilus edlis*) Using Papain and Tyrosinase," Biomacromolecules, 15, (2014), pp. 3206-3212.
Van, C.G. et al., "Formation of Dihydroxyphenylalanine From Tyrosine by Coupled Oxidation with Ascorbic Acid," The Journal of Investigative Dermatology, (1949), pp. 11-17.
International Search Report and Written Opinion for International Application No. PCT/US2019/047639, dated Nov. 18, 2019.

\* cited by examiner

PROTEIN-BASED ADHESIVE AND ITS MODIFICATION

CROSS-REFERENCE TO RELATED APPLICATION

This present U.S. patent application is a national stage entry under 35 U.S.C. § 371(b) of International Application No. PCT/US19/47639, filed on Aug. 22, 2019, which relates to and claims the benefits and priority of U.S. Provisional Application Ser. No. 62/721,112, filed Aug. 22, 2018, the contents of which are incorporated herein by reference in their entirety.

GOVERNMENT RIGHTS

This invention was made with Government support under DMR1309787, awarded by the National Science Foundation. The Government has certain rights in the invention.

STATEMENT OF SEQUENCE LISTING

A computer-readable form (CRF) of the Sequence Listing is submitted with this application. The file, generated on Aug. 21, 2019, is entitled 68335-02_ST25_txt, the contents of which are incorporated herein in their entirety. Applicant states that the content of the computer-readable form is the same and the information recorded in computer readable form is identical to the written sequence listing.

TECHNICAL FIELD

This invention relates to protein-based adhesives that are capable to adhere to a substrate in a dry, wet, moist, or an aqueous environment, particularly, to adhesives comprising a crosslinking agent and an elastin-like polypeptide (ELP) that contain tyrosine, lysine, cysteine, dihydroxyphenylalanine (DOPA) or trihydroxyphenylalanine (TOPA) amino acid residue, or a combination thereof, on the polypeptide chain. Among others, the adhesives disclosed herein may find various applications in medical treatments or surgical operations.

BACKGROUND

This section introduces aspects that may help facilitate a better understanding of the disclosure. Accordingly, these statements are to be read in this light and are not to be understood as admissions about what is or is not prior art.

There has been a wealth of recent interest in the development of adhesive materials that function in wet or underwater environments. In particular, much of this focus has been placed on adhesive development for biomedical applications, as a suitable biomedical adhesive could have an immense impact on health and the economy. Each year, over 230 million major surgeries are performed worldwide, and over 12 million traumatic wounds are treated in the U.S. alone. Approximately 60% of these wounds are closed using mechanical methods such as sutures and staples. Sutures and staples have several disadvantages relative to adhesives, including patient discomfort, higher risk of infection, and the inherent damage to surrounding healthy tissue.

Current FDA-approved adhesives and sealants face several challenges. First, numerous adhesives exhibit toxic characteristics. For example, cyanoacrylate-based adhesives like Dermabond® and SurgiSeal® can only be applied topically due to carcinogenic degradation products. Fibrin sealants like TISSEEL® and ARTISS® are derived from blood sources and therefore carry the potential for blood-borne pathogen transmission. Poly(ethylene glycol) (PEG) adhesives are approved as a suture sealants but, due to intense swelling when wet, have the potential to cause moderate inflammatory responses. TissuGlu®, a following subcutaneous implantation, and, in clinical trials, seroma formation occurred in 22% of patients. More important, however, is that most of these adhesives do not possess strong adhesion in an excessively wet environment and are not approved for application in wound closure. In fact, many of these materials specifically advise to dry the application area as much as possible.

In approaching the challenge of developing a strong adhesive for wet applications, many researchers have been inspired by natural glues. Specifically, underwater application and bonding has been demonstrated with materials based on organisms such as sandcastle worms and mussels. Both of these organisms produce proteins containing the non-canonical amino acid 3,4-dihydroxyphenylalanine (DOPA), which has been shown to provide adhesion strength, even in wet environments. In the case of a mussel-mimetic polymer, underwater application was achieved by dissolving the polymer in a chloroform/methanol solution to maintain phase separation from the aqueous environment. The use of toxic organic solvents, however, is not appropriate for biomedical applications.

An alternative method for underwater application uses the phenomenon of coacervation, a form of aqueous liquid-liquid phase separation that is implicated in the adhesion mechanism of sandcastle worms, caddisfly larvae, and mussels. Adhesive coacervate materials mimicking both mussels and sandcastle worms have been developed. To form these coacervates, multiple components needed to be mixed in specific conditions and thus limited their overall applicability.

As it can be seen, there is a need for a strong adhesive that functions in a wet environment. It would also be desirable if this adhesive could be manipulated in forming a strong seal in the desired environment. It would be further desirable if the adhesive was also non-toxic and may be used in biomedical applications.

BRIEF SUMMARY

The present disclosure provides protein-based adhesives that are capable to adhere to a substrate in a dry, wet, moist or even an aqueous environment. Particularly, said adhesives comprise a crosslinking agent and an elastin-like polypeptide (ELP) that contain tyrosine, lysine, cysteine, dihydroxyphenylalanine (DOPA) or trihydroxyphenylalanine (TOPA) amino acid residue, or a combination thereof, on the polypeptide chain of ELP. The ELP-based adhesives of the present disclosure show high cytocompatability and are appropriate for use in biomedical applications, including broad applications in medical operations or surgeries.

In some embodiments, the present disclosure provides protein-based adhesives that are capable to adhere to a substrate in a dry, wet, moist or an aqueous environment. Particularly, the physical and chemical properties, including the cure time and strength, of said adhesives comprising a crosslinking agent and an elastin-like polypeptide (ELP) that contain tyrosine, lysine, cysteine, dihydroxyphenylalanine (DOPA) or trihydroxyphenylalanine (TOPA) amino acid residue, or a combination thereof, on the polypeptide chain of ELP, may be modified and controlled by adjusting the type and amount of said crosslinking agent.

In some illustrative embodiments, the present invention relates to an adhesive comprising a crosslinking agent and an elastin-like polypeptide (ELP), wherein polypeptide chain of said ELP contains tyrosine, lysine, cysteine, dihydroxyphenylalanine (DOPA) or trihydroxyphenylalanine (TOPA) amino acid residue, or a combination thereof.

In some other embodiments, the present invention relates to an adhesive comprising a crosslinking agent, an elastin-like polypeptide (ELP), wherein polypeptide chain of said ELP contains tyrosine, lysine, cysteine, dihydroxyphenylalanine (DOPA) or trihydroxyphenylalanine (TOPA) amino acid residue, or a combination thereof, and an oxidizing agent.

In some illustrative embodiments, the present invention relates to an adhesive disclosed herein, wherein said oxidizing agent comprises a ferric salt, hydrogen peroxide, sodium periodate, or an enzyme that transforms the phenolic side chain of tyrosine residues of said ELP.

In some illustrative embodiments, the present invention relates to an adhesive disclosed herein, wherein said DOPA of polypeptide chain of said ELP is generated by using a tyrosinase.

In some illustrative embodiments, the present invention relates to an adhesive disclosed herein, wherein said adhesive is capable of adhering to a substrate when applied to said substrate in a dry, wet, moist, or an aqueous environment.

In some illustrative embodiments, the present invention relates to an adhesive disclosed herein, wherein said adhesive is compatible for biomedical applications.

In some illustrative embodiments, the present invention relates to an adhesive disclosed herein, wherein said adhesive is useful in medical treatments or surgical operations.

In some illustrative embodiments, the present invention relates to an adhesive disclosed herein, wherein said crosslinking agent is an oxidizing agent.

In some illustrative embodiments, the present invention relates to an adhesive disclosed herein, wherein said oxidizing agent comprises a ferric salt, hydrogen peroxide, sodium periodate, or an enzyme that transforms the phenolic side chain of tyrosine residues of said ELP.

In some illustrative embodiments, the present invention relates to an adhesive disclosed herein, wherein said crosslinking agent comprises trishydroxymethylphosphine (THP), tetrakis(hydroxymethyl)phosphonium chloride (THPC), an N-hydroxysuccinyl ester (NHS), genipin, pyridyl disulfide, a maleimide, a vinylsulfone, a haloacetyl, or a combination thereof.

In some illustrative embodiments, the present invention relates to a method of manufacturing an adhesive comprising the steps of:

providing a crosslinking agent; and providing an elastin-like polypeptide (ELP), wherein polypeptide chain of said ELP contains tyrosine, lysine, cysteine, dihydroxyphenylalanine (DOPA) or trihydroxyphenylalanine (TOPA) amino acid residue, or a combination thereof.

In some illustrative embodiments, the present invention relates to a method of manufacturing an adhesive disclosed herein, wherein the method further comprises a step of adding an oxidizing agent.

BRIEF DESCRIPTION OF DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1:
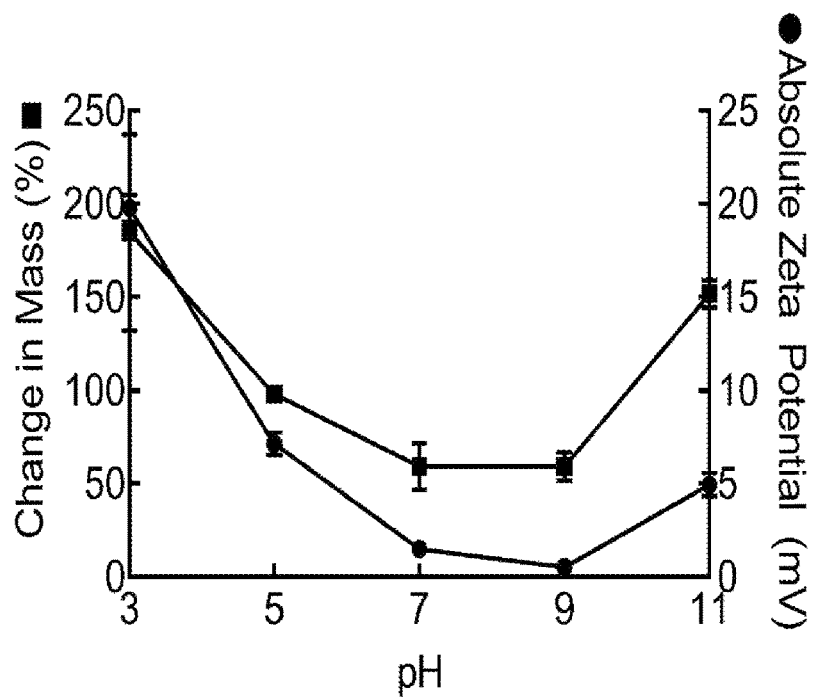
FIG. 1, changes occur in the mass of YKV hydrogels after swelling across a range of pH (square marker) and absolute zeta potential of YKV solution across a range of pH (circle marker). YKV was crosslinked into hydrogels using THP. Zeta potential is a measure of overall surface charge of a protein. Actually, a change in mass less than 100% indicates a shrinking. The hydrogels tended to shrink at pH where the overall charge (zeta potential) was low. Shrinking near physiological pH is useful for surgical adhesives, as it reduces the risk of pressure on nearby tissues, blood vessels, and nerves.

It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 20%, within 10%, within 5%, or within 1% of a stated value or of a stated limit of a range.

In the present disclosure the term "substantially" can allow for a degree of variability in a value or range, for example, within 80%, within 90%, within 95%, or within 99% of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "patient" includes human and non-human animals such as companion animals (dogs and cats and the like) and livestock animals. Livestock animals are animals raised for food production. The patient to be treated is preferably a mammal, in particular a human being.

For reference, the following amino acid abbreviations and names may be identified herein as applying to one or more polypeptides or proteins of the present disclosure:

| Three-letter Abbreviation | Single-letter Abbreviation | Amino Acid Name |
|---|---|---|
| Ala | A | Alanine |
| Arg | R | Arginine |
| Asn | N | Asparagine |
| Asp | D | Aspartic acid (Aspartate) |
| Cys | C | Cysteine |
| Gln | Q | Glutamine |
| Glu | E | Glutamic acid (Glutamate) |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |
| Thr | T | Threonine |
| Trp | W | Tryptophan |
| Tyr | Y | Tyrosine |
| Val | V | Valine |
| Asx | B | Aspartic acid or Asparagine |
| Glx | Z | Glutamine or Glutamic acid |
| Xaa | X | (any amino acid, or a group of amino acids, as may be referenced herein) |

Broadly speaking, the present disclosure provides protein-based adhesives that are capable to adhere to a substrate in a dry, wet, moist or even an aqueous environment. Particularly, said adhesives comprise a crosslinking agent and an elastin-like polypeptide (ELP) that contain tyrosine, lysine, cysteine, dihydroxyphenylalanine (DOPA) or trihydroxyphenylalanine (TOPA) amino acid residue, or a combination thereof, on the polypeptide chain of ELP. The ELP-based adhesives of the present disclosure show high cytocompatability and are appropriate for use in biomedical applications, including broad applications in medical operations or surgeries. Compositions and methods of use are within the scope of this application.

In some embodiments, the present disclosure provides protein-based adhesives that are capable to adhere to a substrate in a dry, wet, moist or an aqueous environment. Particularly, the physical and chemical properties, including the cure time and strength, of said adhesives comprising a crosslinking agent and an elastin-like polypeptide (ELP) that contain tyrosine, lysine, cysteine, dihydroxyphenylalanine (DOPA) or trihydroxyphenylalanine (TOPA) amino acid residue, or a combination thereof, on the polypeptide chain of ELP, may be modified and controlled by adjusting the type and amount of said crosslinking agent.

In some embodiments, an oxidizing agent is a crosslinking agent. In some other embodiments, a crosslinking agent is an oxidizing agent. In some embodiment, a crosslinking agent is usually incorporated in the final network of the adhesive, while an oxidizing agent may or may not be incorporated in the final network of the adhesive. For example, THP act as a crosslinker because they are incorporated into the final network of said adhesive. On the other hand, periodate, acts as an oxidizer to the protein to the crosslinking process, but they are not incorporated into the final network of the adhesive. Iron acts as both an oxidizer and a crosslinker because it does oxidize the protein, and it is also incorporated into the final network.

In some illustrative embodiments, the present invention relates to an adhesive comprising a crosslinking agent and an elastin-like polypeptide (ELP), wherein polypeptide chain of said ELP contains tyrosine, lysine, cysteine, dihydroxyphenylalanine (DOPA) or trihydroxyphenylalanine (TOPA) amino acid residue, or a combination thereof.

In some other embodiments, the present invention relates to an adhesive comprising a crosslinking agent, an elastin-like polypeptide (ELP), wherein polypeptide chain of said ELP contains tyrosine, lysine, cysteine, dihydroxyphenylalanine (DOPA) or trihydroxyphenylalanine (TOPA) amino acid residue, or a combination thereof, and an oxidizing agent.

In some illustrative embodiments, the present invention relates to an adhesive disclosed herein, wherein said oxidizing agent comprises a ferric salt, hydrogen peroxide, sodium periodate, or an enzyme that transforms the phenolic side chain of tyrosine residues of said ELP.

In some illustrative embodiments, the present invention relates to an adhesive disclosed herein, wherein said DOPA of polypeptide chain of said ELP is generated by using a tyrosinase.

In some illustrative embodiments, the present invention relates to an adhesive disclosed herein, wherein said adhesive is capable of adhering to a substrate when applied to said substrate in a dry, wet, moist, or an aqueous environment.

In some illustrative embodiments, the present invention relates to an adhesive disclosed herein, wherein said adhesive is compatible for biomedical applications.

In some illustrative embodiments, the present invention relates to an adhesive disclosed herein, wherein said adhesive is useful in medical treatments or surgical operations.

In some illustrative embodiments, the present invention relates to an adhesive disclosed herein, wherein said crosslinking agent is an oxidizing agent.

In some illustrative embodiments, the present invention relates to an adhesive disclosed herein, wherein said oxidizing agent comprises a ferric salt, hydrogen peroxide, sodium periodate, or an enzyme that transforms the phenolic side chain of tyrosine residues of said ELP.

In some illustrative embodiments, the present invention relates to an adhesive disclosed herein, wherein said crosslinking agent comprises trishydroxymethylphosphine (THP), tetrakis(hydroxymethyl)phosphonium chloride (THPC), an N-hydroxysuccinyl ester (NHS), genipin, pyridyl disulfide, a maleimide, a vinylsulfone, a haloacetyl, or a combination thereof.

In some illustrative embodiments, the present invention relates to a method of manufacturing an adhesive comprising the steps of:
providing a crosslinking agent; and
providing an elastin-like polypeptide (ELP), wherein polypeptide chain of said ELP contains tyrosine, lysine, cysteine, dihydroxyphenylalanine (DOPA) or trihydroxyphenylalanine (TOPA) amino acid residue, or a combination thereof.

In some illustrative embodiments, the present invention relates to a method of manufacturing an adhesive disclosed herein, wherein the method further comprises a step of adding an oxidizing agent.

In some illustrative embodiments, the present invention relates to a method of manufacturing an adhesive disclosed herein, wherein said oxidizing agent comprises a ferric salt, hydrogen peroxide, sodium periodate, or an enzyme that transforms the phenolic side chain of tyrosine residues of said ELP.

In some illustrative embodiments, the present invention relates to a method of manufacturing an adhesive disclosed herein, wherein said crosslinking agent is trishydroxymethylphosphine (THP), tetrakis(hydroxymethyl)phosphonium chloride (THPC), an N-hydroxysuccinyl ester (NHS), genipin, pyridyl disulfide, a maleimide, a vinylsulfone, a haloacetyl, or a combination thereof.

In some illustrative embodiments, the present invention relates to a method of manufacturing an adhesive disclosed herein, wherein said adhesive is capable of adhering to a substrate when applied to said substrate in a dry, wet, moist, or an aqueous environment.

In some illustrative embodiments, the present invention relates to a method of manufacturing an adhesive disclosed herein, wherein said adhesive is useful in medical treatments or surgical operations.

In some illustrative embodiments, the present invention relates to a method of manufacturing an adhesive disclosed herein, wherein said DOPA of polypeptide chain of said ELP is generated by using a tyrosinase.

In some illustrative embodiments, the present invention relates to a method of manufacturing an adhesive disclosed herein, wherein said adhesive is capable of adhering to a substrate when applied to said substrate in a dry, wet, moist, or aqueous environment.

In another embodiment of the present disclosure, the ELPs comprise tyrosine, lysine or cysteine residues. In other embodiments, some or all of the tyrosine residues are replaced by DOPA and/or TOPA, in any combination thereof. The DOPA and TOPA may be formed enzymatically through treatment with an enzyme such as a tyrosinase of ELP polypeptides containing tyrosine residues. Alternative, they may be formed chemically using methods well known in the art. Another method would be to produce the ELPs synthetically, adding DOPA and TOPA to the peptides. Yet in some other embodiments, the ELPs of the present disclosure may be produced recombinantly using methods known in the art, substituting DOPA and/or TOPA for the tyrosine.

Certain embodiments of the present disclosure may be better understood through the following non-limiting examples.

Many "smart" materials have been designed to respond to environmental triggers such as temperature, light, and pH. Smart materials are especially useful in applications like controlled drug release, tissue engineering, and microfluidics, where changes in pH or temperature can be harnessed to regulate or affect surrounding systems. Hydrogels are commonly used as a material for these systems due to their biocompatibility, softness, and controlled permeability to small molecules. The softness of hydrogels can be tuned by changing the crosslinked network's density. If the hydrogel was made with a chemical crosslinker, the density can be tuned by changing the concentration of crosslinker. pH-sensitivity can be induced in hydrogels by including ionizable functional groups. When a gel has a higher charge, it is more hydrophilic and will swell and soften due to attracted water. When the gel has a charge close to neutral, it will become more hydrophobic and expel water while shrinking and stiffening. These pH-sensitive hydrogels can be made from synthetic or natural polymers. Engineered natural polymers like recombinant proteins allow for precise sequence control and lower dispersity than synthetic polymer systems.

Non-uniform populations in pH-sensitive charged systems could cause shifts in charge to be less distinct since the more diverse polymer population does not have a homogeneous response. Uniform populations like recombinant proteins are more likely to have a homogeneous response to environmental changes. Additionally, recombinant protein systems allow for tighter control over small changes in charge since very similar proteins can be made that only differ by a few amino acids. Recombinant proteins can also be designed to contain modular protein "tags" that add functionality to the protein, including purification, identification, and environmental sensitivity. Elastin-like polypeptides (ELPs) are recombinant mimics of native elastin with similar elastic properties, and improved solubility. ELPs are composed of the repeating pentapeptide sequence VPGXG (SEQ ID NO: 11), where X is any amino acid except proline. ELPs are well-studied elastomeric proteins that are hydrophilic, biocompatible, and easy to produce in large quantities. ELPs can also hase separate upon heating above the lower critical solution temperature (LCST). ELP-based hydrogels are elastic, highly resilient, and can be tuned to the stiffness range of soft tissues. Ionizable amino acids have been used to induce pH sensitivity in uncrosslinked ELPs. LCST behavior of ELPs is driven by interactions with water, and ELPs that are more hydrophilic have higher LCSTs. When ionizable amino acids were incorporated into ELP proteins, the LCST of the protein became pH sensitive. If the ELP was in solution at a pH where the ionizable amino acid was charged, the ELP became more hydrophilic. This caused the LCST of the ELP to increase. Recombinant proteins and synthetic polymers that are pH sensitive can remain pH sensitive after crosslinking. Polymer-based hydrogels containing polar molecules show pH-dependent swelling and mechanical properties. If the polar groups in these hydrogels are blocked through chemical modification, the gel will become more hydrophobic and thus experience lower swelling ratios and higher stiffness. In particular, acetylation can be used to block lysine and tyrosine groups.

MATERIALS AND METHODS

This present disclosure is a further development of the subject matter technology of our previous U.S. patent application Ser. No. 15/230,762, filed Aug. 8, 2016, the content which is incorporated hereby into the instant application in its entirety.

Reagents: All chemicals were purchased from Sigma-Aldrich (St. Louis, MO) or Avantor Performance Materials (Center Valley, PA) unless stated otherwise. Water was ultra-purified with a Milli-Q ultra-purification system (Millipore, Billerica, MA). NIH/3T3 fibroblasts were a generous gift from Dr. Alyssa Panitch (Purdue University). TISSEEL® was generously donated by Baxter BioSurgery (Deerfield, IL).

The method of preparing various ELP proteins and their characterization was reported in the U.S. patent application Ser. No. 15/230,762, filed Aug. 8, 2016, and is further elaborated below. A new variation has been developed, which contains thiol groups from cysteine guest residues. In this document, "YKV" refers to an ELP protein containing equal amounts of Y, K, and V in its guest residue positions, and "mYKV" refers to the same protein that has been modified to include DOPA.

The proteins are dissolved into water or phosphate-buffered saline at varying concentrations. Coacervate is isolated by dissolving protein into a solvent, heating the solution, and centrifuging the solution. The supernatant (protein-poor layer) is removed and the remaining coacervate (protein-rich layer) is used for testing. The protein solutions were mixed with the following chemicals for the following effects: Tris-hydroxymethyl phosphine (THP), (or tris-hydroxymethyl phosphonium chloride THPC) which chemically binds to amine groups in the protein (and potentially to amines in the surface of biological tissues). The addition of THP can create a crosslinked hydrogel in the presence or absence of DOPA. The amount of THP added affects the stiffness, swelling, and water content of the resulting hydrogel. If THP is added to a protein containing DOPA, it can also improve adhesive strength. This may occur through the binding of the protein to itself and to the surface of the tissue.

Iron (iron nitrate nonahydrate) (or various other metal ions), which chelates with DOPA groups. When iron is mixed with DOPA-containing proteins, three DOPA groups chelate with one iron molecule. The chelated DOPA can then covalently bind to other chelated DOPA to form bonds within the proteins, or the chelated DOPA can covalently bind to surfaces. Sodium periodate (or other oxidizers), which oxidizes DOPA and causes it to become more reactive. Oxidized DOPA is more likely to form cohesive bonds. Hydrogen peroxide (or other oxidizers), which oxidizes thiol groups and cause them to bind to other thiol groups.

TISSEEL® (by Baxter International Inc.) was used as a comparison in adhesive testing. TISSEEL® is a protein based sealant used to prevent the leaking of fluid from sutured wounds inside of the body. It is not used for wound closure without the use of mechanical support, but is a commonly used commercial product for comparison in adhesive testing.

To measure the swelling of hydrogels, protein solution was mixed with THP and put into a custom mold. After crosslinking, the hydrogel was submerged in a pH-controlled liquid, and the mass of the hydrogel was monitored over time. After seven days, the hydrogel was removed and dried and its dry mass was measured. Swelling ratio and water content were calculated as:

$$\text{Swelling Ratio} = \frac{m_w}{m_d}$$

$$\text{Water Content } (\%) = 100 \times \frac{m_w - m_d}{m_w}$$

$m_d$ = mass of dried hydrogel $m_w$ = mass of swollen hydrogel

The stiffness of hydrogels was measured by compressing hydrogels at a fixed rate and calculating the slope of the stress-strain curve between 5 and 20% strain.

Adhesive strength was measured with lap-shear adhesion. Aluminum or pig skin substrates were used, and the samples were applied to adherends and cured in a 37° C. humid environment until testing. To test, a constant force was applied and the adhesive strength was calculated as the maximum force before failure divided by the overlap area of the adherends. Samples that failed when handled before testing were not measured, and the failure rate on handling is shown below each figure in a table inset. Unless noted otherwise, six replicates were created for each group. If a group had two or fewer samples that were tested (i.e. did not fail upon handling), the group is shown without an error bar and is excluded from statistical analysis.

Pig skin adhesion was based on ASTM standard F2255-05. Testing adherends were prepared by cutting pig skin (supplier) into squares and storing at −80° C. until use. Custom aluminum adherends were made with a 1.2×1.2 cm squares cut out. Pig skin was thawed in PBS and applied to aluminum adherends using cyanoacrylate glue. To prepare adhesive, protein was dissolved in water at the desired concentration and the pH was adjusted to 7.4±0.1 using sodium hydroxide and hydrochloric acid. Crosslinker solutions were prepared in water at concentrations necessary to reach the desired ratio to the reactive group in YKV. All solutions were kept on ice during use. 10 µL of protein solution was applied to one pig skin adherend face. If used, 5 µL of crosslinker was applied on top of the protein solution. The other pig skin adherend was immediately applied on top of the protein solution. The sample was covered in a water moistened paper towel and weighted with a mass of 50 grams. The samples were placed into a humid chamber and incubated at 37° C. for the necessary time. Humid chambers were removed from the incubator 30 minutes before testing to allow the samples to come to room temperature without drying out. Samples were loaded into a BOSE Electroforce® 3200 series III, and pulled at a constant rate of 2 mm/min until failure. Overlap area was measured with calipers. Adhesive strength was calculated as the maximum force divided by overlap area, and toughness was calculated as the area under the stress-strain curve divided by overlap area. Six replicates of each group were prepared unless noted otherwise.

If two groups were compared, a two-sample t-test was used and statistical significance is noted by *($p<0.05$) or **($p<0.01$). If more than two groups were compared, ANOVA was used. If the variance was equal, Tukey groupings were used. If the variance was unequal, Games-Howell groupings were used. Groupings are noted by the use of letters, where groups that do not share a letter are statistically different ($p<0.05$).

Protein [YKV-48], also known as EL(YKV)16 or ELY$_{16}$. SEQ ID NO: 1 (DNA) and SEQ ID NO: 2 (protein) in the CRF file of 68335-02_ST25.txt Amino acid sequence:

(SEQ ID NO: 2)
MMASMTGGQQMGHHHHHHHDDDDKLDGTLPGYGVPGKGVPGVGVPGYGVP

GKGVPGVGVPGYGVPGKGVPGVGVPGYGVPGKGVPGVGVPGYGVPGKGVP

GVGVPGYGVPGKGVPGVGVPGYGVPGKGVPGVGVPGYGVPGKGVPGVGVP

GYGVPGKGVPGVGVPGYGVPGKGVPGVGVPGYGVPGKGVPGVGVPGYGVP

-continued

GKGVPGVGVPGYGVPGKGVPGVGVPGYGVPGKGVPGVGVPGYGVPGKGVP

GVGVPGYGVPGKGVPGVGVPVADRGMRLE

Protein [YKV-72], SEQ ID NO: 3 (DNA) and SEQ ID NO: 4 (protein) in the CRF file of 68335-02_ST25.txt Amino acid sequence:

(SEQ ID NO: 4)
MMASMTGGQQMGHHHHHHHDDDDKLDGTLPGYGVPGKGVPGVGVPGYGVP

GKGVPGVGVPGYGVPGKGVPGVGVPGYGVPGKGVPGVGVPGYGVPGKGVP

GVGVPGYGVPGKGVPGVGVPGYGVPGKGVPGVGVPGYGVPGKGVPGVGVP

GYGVPGKGVPGVGVPGYGVPGKGVPGVGVPGYGVPGKGVPGVGVPGYGVP

GKGVPGVGVPGYGVPGKGVPGVGVPGYGVPGKGVPGVGVPGYGVPGKGVP

GVGVPGYGVPGKGVPGVGVPGYGVPGKGVPGVGVPGYGVPGKGVPGVGVP

GYGVPGKGVPGVGVPGYGVPGKGVPGVGVPGYGVPGKGVPGVGVPGYGVP

GKGVPGVGVPGYGVPGKGVPGVGVPGYGVPGKGVPGVGVPVADRGMRLE

Protein [YKV-96], SEQ ID NO: 5 (DNA) and SEQ ID NO: 6 (protein) in the CRF file of 68335-02_ST25.txt Amino acid sequence:

(SEQ ID NO: 6)
MMASMTGGQQMGHHHHHHHDDDDKLDGTLPGYGVPGKGVPGVGVPGYGVP

GKGVPGVGVPGYGVPGKGVPGVGVPGYGVPGKGVPGVGVPGYGVPGKGVP

GVGVPGYGVPGKGVPGVGVPGYGVPGKGVPGVGVPGYGVPGKGVPGVGVP

GYGVPGKGVPGVGVPGYGVPGKGVPGVGVPGYGVPGKGVPGVGVPGYGVP

GKGVPGVGVPGYGVPGKGVPGVGVPGYGVPGKGVPGVGVPGYGVPGKGVP

GVGVPGYGVPGKGVPGVGVPGYGVPGKGVPGVGVPGYGVPGKGVPGVGVP

GYGVPGKGVPGVGVPGYGVPGKGVPGVGVPGYGVPGKGVPGVGVPGYGVP

GKGVPGVGVPGYGVPGKGVPGVGVPGYGVPGKGVPGVGVPGYGVPGKGVP

GVGVPGYGVPGKGVPGVGVPGYGVPGKGVPGVGVPGYGVPGKGVPGVGVP

GYGVPGKGVPGVGVPGYGVPGKGVPGVGVPGYGVPGKGVPGVGVPGYGVP

GKGVPGVGVPVADRGMRLE

Protein [YKV-48] without tags (also known as HD0-EL(YKV)16), SEQ ID NO: 7 (DNA) and SEQ ID NO: 8 (protein) in the CRF file of 68335-02_ST25.txt Amino acid sequence:

(SEQ ID NO: 8)
MSKGPGVDGTLPGYGVPGKGVPGVGVPGYGVPGKGVPGVGVPGYGVPGKG

VPGVGVPGYGVPGKGVPGVGVPGYGVPGKGVPGVGVPGYGVPGKGVPGVG

VPGYGVPGKGVPGVGVPGYGVPGKGVPGVGVPGYGVPGKGVPGVGVPGYG

VPGKGVPGVGVPGYGVPGKGVPGVGVPGYGVPGKGVPGVGVPGYGVPGKG

VPGVGVPGYGVPGKGVPGVGVPGYGVPGKGVPGVGVPGYGVPGKGVPGVG

VPVADRGMRLDKEFLE

Protein [CKVYKV-72], SEQ ID NO: 9 (DNA) and SEQ ID NO: 10 (protein) in the CRF file of 68335-02_ST25.txt Amino acid sequence:

(SEQ ID NO: 10)
MSKGPGVDGTLPGYGVPGKGVPGVGVPGCGVPGKGVPGVGVPGYGVPGKG

VPGVGVPGCGVPGKGVPGVGVPGYGVPGKGVPGVGVPGCGVPGKGVPGVG

VPGYGVPGKGVPGVGVPGCGVPGKGVPGVGVPGYGVPGKGVPGVGVPGCG

VPGKGVPGVGVPGYGVPGKGVPGVGVPGCGVPGKGVPGVGVPGYGVPGKG

VPGVGVPGCGVPGKGVPGVGVPGYGVPGKGVPGVGVPGCGVPGKGVPGVG

VPGYGVPGKGVPGVGVPGCGVPGKGVPGVGVPGYGVPGKGVPGVGVPGCG

VPGKGVPGVGVPGYGVPGKGVPGVGVPGCGVPGKGVPGVGVPGYGVPGKG

VPGVGVPGCGVPGKGVPGVGVPVADRGMRLEHHHHHH

Proteins were constructed with a cloning scheme adapted from one previously developed by our lab. ELP[YKV-48] was constructed as previously described. The modified scheme used AgeI and AvaI restriction enzymes (New England Biolabs, Ipswich MA) to create uninterrupted repeats of the ELP pentapeptide sequence. To construct HD0-ELP[YKV-48], pET21b plasmid was first modified by removing the T7-tag and His-tag followed by inserting a DNA oligo encoding amino acid sequence Ser-Lys-Gly-Pro-Gly (SEQ ID NO: 12). The previously cloned ELP[YKV-48] encoding DNA fragment was then inserted into the modified pET21b after the leading sequence. Standard molecular cloning techniques were used. Proteins were expressed using E. coli Rosetta™ 2(DE3) pLysS (Novagen, Burlington MA) bacterial expression strains. ELP[YKV-48] was expressed as previously described. Cells were initially cultured for 14 h overnight at 37° C. in 2×YT medium using the appropriate antibiotics. For ELP[YKV-48], overnight cell cultures were then diluted 1:25 into a fermentor (BioFlo 100, 14 L capacity, New Brunswick Scientific, Enfield CT) with 10 L of Terrific Broth using the appropriate antibiotics. At an optical density (OD) of 4-5, protein expression was induced using 2.5 mM isopropyl β-D-1-thiogalactopyranoside (IPTG, VWR, Radnor PA). Fermentation continued until the OD was ~10. Cells were then harvested by centrifugation at 4° C. For HD0-ELP[YKV-48], overnight cell cultures were diluted 1:100 into 4 L flasks containing 1 L of 2×YT medium and the appropriate antibiotics. At an OD of ~1, protein expression was induced using 1 mM IPTG. After 3.5 h of additional culture, cells were harvested by centrifugation at 4° C. Both proteins were purified as described previously. Expression and purification were confirmed with SDS-PAGE imaging (FIG. 4B).

Standard molecular cloning techniques were used. YKV proteins were expressed using E. coli Rosetta™ 2(DE3) pLysS (Novagen, Burlington MA) bacterial expression strains as previously described. Cells were initially cultured for 14 h overnight at 37° C. in 2×YT medium using the appropriate antibiotics. Overnight cell cultures were then diluted 1:25 into a fermentor (BioFlo 100, 14 L capacity, New Brunswick Scientific, Enfield CT) with 10 L of Terrific Broth using the appropriate antibiotics. At an optical density (OD) of 4-5, protein expression was induced using 2.5 mM isopropyl β-D-1-thiogalactopyranoside (IPTG, VWR, Radnor PA). Fermentation continued until the OD was ~10. Cells were then harvested by centrifugation at 4° C. YKV was purified as described previously. Expression and purification were confirmed with SDS-PAGE and Western Blot imaging. Modified EL YKV was produced by mushroom tyrosinase reaction, purification.

Hydrogel Formation

Protein was dissolved into 200 mM buffer composed of 80 mM citric acid (MP Biomedicals, Santa Ana CA), 40 mM sodium phosphate dibasic (Sigma Aldrich, St. Louis MO), 40 mM 1,3-bis(tris(hydroxymethyl)methylamino)propane (Alfa Aesar, Haverhill MA), and 40 mM N-cyclohexyl-3-aminopropanesulfonic acid (Sigma Aldrich) in Milli-Q® filtered water, pH 7. Hereafter this buffer mixture is referred to as CPPC buffer. Tris(hydroxymethylphosphine) (THP, Acros Organics, Geel, Belgium) was dissolved into 200 mM CPPC buffer (pH 7). Protein solution (13 wt % final oncentration) and crosslinker solution were added at a 9:1 volume ratio and crosslinked in a custom silicone mold at 15° C. for 18 h. Gels for swelling tests were 0.8 mm thick and 4 mm in diameter, and gels for mechanical testing were 1.4 mm thick and 4 mm in diameter. After crosslinking, gels were removed from molds and briefly rinsed in water.

Chemical Modification

To acetylate protein in solution, lyophilized protein was dissolved at 14 wt % into 0.05 M sodium borate (MP Biomedical) at pH 9.8. Acetic anhydride (Alfa Aesar) was added at 1000×excess of acetic anhydride to amine groups. After reacting for 18 h at 4° C., the solution was diluted to 10 mg/mL using water and dialyzed against water. The solution was then lyophilized. To acetylate crosslinked hydrogels, gels were swelled in 0.05 M sodium borate buffer at pH 9.8 for at least 5 h. Gels were then immersed in acetic acid at 1000× excess of acetic anhydride to amine groups. After reacting for 18 h at 4° C., gels were rinsed for 5 min in 1 mL of water, rinsed for 5 min in 1 mL of the required buffer, and then immersed in 4 mL of the required buffer for further testing.

Protein Sequence and Charge Modification Matrix-assisted laser desorption/ionization time of flight (MALDI-TOF) was performed on lyophilized, uncrosslinked protein (Purdue University Center for Cancer Research). Amino acid analysis was completed on lyophilized, uncrosslinked protein and on lyophilized, crosslinked hydrogels (UC Davis Molecular Structure Facility). Electrospray Ionization Mass Spectrometry was completed by Charng-Yu Lin. Amine content was determined using an o-phthalaldehyde (OPA) assay. The assay reagent was composed of 5.96 mM ortho-phthalaldehyde (Alfa Aesar), 342.6 mM ethanol (Decon Labs, King of Prussia PA), 28.4 mM β-mercaptoethanol (Sigma Aldrich), 43.9 mM sodium borate (MP Biomedical), and 34.6 mM sodium dodecyl sulfate (Sigma Aldrich) in Milli-Q® water. 10 μL of a protein and Milli-Q® water solution was mixed with 300 μL of assay reagent. After 10 min of incubation, samples were measured with an excitation at 350 nm and an emission at 455 nm. ELP[YKV-48] was used to construct a standard curve. Tyrosine content was determined by measuring the autofluorescence of tyrosine residues. Protein solutions dissolved in Milli-Q® water were measured with an excitation at 276 nm and an emission at 305 nm. ELP[YKV-48] was used to construct a standard curve. Zeta potential was measured using a Malvern Zetasizer Nano ZS (Malvern Instruments, Malvern, United Kingdom) with a minimum of 10 runs per sample. Protein was dissolved at 0.1957 mM in 10 mM CPPC buffer (200 mM CPPC buffer as previously described, diluted with Milli-Q-Milli-Q® water) pre-adjusted to the required pH using HCl and NaOH. The solution was filtered and then tested for zeta potential.

Protein Design and Cloning: The elastin-like polypeptide (ELP) labeled as $ELY_{16}$ was designed with Geneious software (Biomatters Inc., San Francisco, CA) using the repeated amino acid sequence Val-Pro-Gly-Xaa-Gly (SEQ ID NO: 13); the guest residues Xaa were evenly divided among Tyr, Lys, and Val. The complete amino acid sequence for full-length $ELY_{16}$ may be found in the Sequence Listing concomitantly filed. Cloning was performed using standard techniques (Ausubel F M et al., editors. Current Protocols in Molecular Biology. New York: John Wiley & Sons; 2003) and a scheme modified from one previously developed (Renner, J N et al., Protein Expr Purif 2012; 82:90-6). The new scheme utilized Agel and Aval restriction enzymes (New England Biolabs, Ipswich, MA) to achieve seamless repeats of the elastin-like sequence.

Protein Expression and Purification: $ELY_{16}$ was transformed into the Rosetta™ 2(DE3)pLysS E. coli expression host (EMD Chemicals, Gibbstown, NJ). Bacterial colonies were inoculated into 2×YT medium containing 50 g/mL kanamycin and 34 g/mL chloramphenicol and grown 16-18 h at 37° C. and 300 rpm. The overnight culture was diluted 1:250 for expression in a 14 L-capacity fermenter (BioFlo 100, New Brunswick Scientific, Enfield, CT) with 10 L of Terrific Broth (TB). When the optical density (OD) at 600 nm reached 5-6, protein expression was induced by the addition of isopropyl β-D-1-thiogalactopyranoside (IPTG, EMD Chemicals) at a final concentration of 2.5 mM. Upon reaching stationary phase, cells were harvested by centrifugation and immediately resuspended in Buffer B (8 M urea, 100 mM $NaH_2PO_4$, 100 mM Tris-Cl, pH 8.0) before being frozen at −80° C.

Purification was performed by a salting and heating method that was modified from a previously described protocol (Renner, J N et al., Biomacromolecules 2012; 13:3678-85; Kim, Y et al., Biomater Sci 2014; 2:1110-9). Cells were lysed by multiple freeze-thaw cycles in combination with sonication (Misonix XL-2000, Qsonica, Newtown, CT) for 1 min followed by a 1 min incubation on ice. Total sonication time was at least 2 h. The cell lysate was then centrifuged at 10000 g for 45 min and 4° C. to remove the cell debris. To salt out undesired proteins, 10% (w/v) ammonium sulfate was added to the cleared supernatant. The mixture was incubated on ice for 310 min followed by centrifugation for 45 min at 10000 g and 4° C. The supernatant was decanted from the pellet, and an additional 10% (w/v) ammonium sulfate was added to precipitate $ELY_{16}$. The solution was incubated on ice and centrifuged as before. The pellet was then resuspended in water at 500 mg/mL based on wet weight, heated to 80° C., vortexed, and heated again to 80° C. The heated solution was centrifuged for 45 min at 10000 g and 25° C., and the supernatant was dialyzed extensively against reverse osmosis water at 10° C. before lyophilization.

Expression and purification of $ELY_{16}$ were confirmed by sodium dodecyl sulfate-polyacrylamide gel electrophoresis (SDS-PAGE) and Western blot using standard techniques (Bonifacino J S et al., editors. Current Protocols in Cell Biology. New York: John Wiley & Sons; 2002). SDS-PAGE gels were stained with Coomassie Brilliant Blue R-250. The protein was detected in the Western blot using an anti-T7 tag antibody conjugated to horseradish peroxidase (EMD Chemicals, Gibbstown, NJ) in combination with a 1-component 3,3',5,5'-tetramethylbenzidine (TMB) colorimetric substrate (Kirkegaard & Perry Laboratories, Gaithersburg, MD). Purity was assessed using densitometry analysis with ImageJ software (NIH, Bethesda, MD) (Abramoff, M D et al., Biophotonics Int 2004; 11:36-41).

The molecular weight was confirmed using matrix-assisted laser desorption/ionization-time of flight (MALDI- TOF) (Dr. Connie Bonham, Campus-Wide Mass Spectrometry Center, Purdue University) with sinapinic acid as the matrix. Briefly, the MALDI mass spectra were obtained on a Voyager DE™-Pro TOF mass spectrometer (Applied Biosystems, Framingham, MA) in the linear mode with delayed extraction. Positive-ion spectra were obtained with an acceleration voltage of 25000 V.

The amino acid composition was verified with amino acid analysis (John Schulze, Molecular Structure Facility, University of California, Davis). Briefly, the sample underwent liquid phase hydrolysis in 2 N HCl/1% phenol at 110° C. for 24 h before being dried. The sample was then dissolved in norleucine dilution buffer to a final volume of 1 mL, vortexed, and spun down. Injection volume was 50 L at a 2.0 nmol scale.

Tyrosinase Modification: To convert tyrosine residues to DOPA, $ELY_{16}$ was dissolved at 2 mg/mL in 0.1 M sodium acetate buffer with 0.1 M ascorbic acid, pH 5.5. Mushroom tyrosinase was added to a final concentration of 150 U/mL, and the mixture was incubated at 37° C. and 200 rpm for 8 h. Enzyme activity was halted with 0.2 mL of 6 N HCl per mL of reaction as described previously (Marumo K & Waite J H, Biochem Biophys Acta 1986; 872:98-103.). The tyrosinase-modified $ELY_{16}$ ($mELY_{16}$) solution was dialyzed extensively in 5% acetic acid at 4° C. and lyophilized.

The extent of conversion was measured with difference spectrophotometry (Waite J H, Anal Chem 1984; 56:1935-9) and comparison to standard solutions of L-DOPA. The increase in molecular weight due to conversion was confirmed by MALDI-TOF and SDS-PAGE. DOPA content was also assessed with amino acid analysis using a procedure similar to that described above with the modifications of using a 5.0 nmol scale and S-2-aminoethyl-L-cysteine as a diluent. The DOPA elution peak was compared with that of an L-DOPA control solution.

Protein Adsorption to Coverslips: Acid-washed coverslips (12 mm diameter, VWR, Radnor, PA) were incubated overnight at 4° C. with $ELY_{16}$, $mELY_{16}$, or bovine serum albumin (BSA, Fraction V, EMD Chemicals, Gibbstown, NJ) dissolved at 1 mg/mL in water. Protein surface density was measured by washing coverslips three times with Milli-Q® water and performing a bicinchoninic acid (BCA) colorimetric assay. Separate standard solutions for $ELY_{16}$ and BSA were used to determine adsorbed protein concentration. Four replicates were tested for each sample.

Cell Culture: NIH/3T3 fibroblasts were generously donated by Dr. Alyssa Panitch (Purdue University). Fibroblasts were cultured at 37° C. and 5% CO2 in high-glucose Dulbecco's Modified Eagle's Medium (DMEM) supplemented with 100 U/mL penicillin-streptomycin (Gibco, Carlsbad, CA) and 10% bovine calf serum. Cells were subcultured at 60-80% confluency.

Cytocompatibility Testing: Coverslips coated in adsorbed protein sterilized by incubation in 70% ethanol for 5 min, blocked in sterile-filtered BSA (1 mg/mL in water) for 30 min, and rinsed with phosphate-buffered saline (PBS, 4.2 mM $NaHPO_4$, 0.8 mM $KH_2PO_4$, 50 mM NaCl, pH 7.4). Fibroblasts were seeded onto coverslips at 2500 cells per $cm^2$ in a 24-well plate (BD Falcon, Durham, NC). For a positive control, acid-washed coverslips were incubated for 5 min in 0.01% poly-L-lysine (PLL, Trevigen, Gaithersburg, MD) then rinsed three times in PBS. Images were taken with a Nikon Ti-E C-1 Plus microscope. All groups were tested in triplicate.

To assess cell viability, cells were cultured for 2 days and tested with a LIVE/DEAD viability/cytotoxicity kit (Molecular Probes, Carlsbad, CA). Cells were incubated in staining solution (1.5 μM ethidium homodimer-1 and 0.5 μM calcein acetoxymethyl ester (calcein AM) in PBS), rinsed three times with PBS, and imaged with a 10× objective. All PBS was supplemented with 0.01% $CaCl_2$) and 0.01% $MgCl_2$ to prevent cell detachment. As a negative control, cells on PLL were incubated in 70% ethanol for 30 min at 37° C. prior to staining. Cells were counted using NIS-ELEMENTS® software (Nikon, Tokyo, Japan), and at least 90 cells were counted per replicate. Viability was calculated as the number of living cells divided by the total number of cells in each replicate.

Cell morphology was assessed via actin staining. After culturing for 2 days, cells were fixed in ice-cold acetone for 1 min and then washed three times with filtered PBS. Coverslips were then incubated for 20 min with Alexa FLUOR®488 phalloidin (Molecular Probes, Carlsbad, CA) at a 1:40 dilution in PBS. Following three 10 min washes with PBS, cells were then counterstained for 30 min with DRAQ5™ (Biostatus Limited, Leicestershire, UK) diluted 1:500 in PBS. Finally, coverslips were rinsed twice in PBS, mounted with VECTASHIELD® (Vector Laboratories), and sealed with nail polish. Confocal imaging was performed with EZ-C1 software using a 40× objective.

Turbidity Testing: Lower critical solution temperatures (LCSTs) of $ELY_{16}$ and $ELY_{16}$ were assessed using turbidity readings from a CRYSTAL16® (Technobis Group, Alkmaar, the Netherlands). Protein samples were held at 10° C. for 15 min, ramped at 1° C./min to 50° C., then held at 50° C. for 2 min. Light transmission data was recorded and normalized to the maximum transmission for each sample. The LCST was calculated as the inflection point of the transmission vs. temperature curve.

Lap Shear Adhesion: Aluminum adherends were prepared and cleaned using ASTM standard D2651-01 (Standard D2651: Preparation of metal surfaces for adhesive bonding. West Conshohocken, PA: ASTM International; 2008). Bulk lap shear adhesion bonding was tested with a modified version of the ASTM D1002 standard, as previously described (Jenkins, C L et al., ACS Appl Mater Interfaces 2013; 5:5091-6; Standard D1002: Apparent shear strength of single-lap-joint adhesively bonded metal specimens by tension loading (metal-to-metal). West Conshohocken, PA: ASTM International; 2010). Briefly, protein was resuspended at 150 mg/mL in water, and 5 L of this solution was spread onto each aluminum adherend. TISSEEL® was prepared according to the manufacturer's instructions and tested by applying an equivalent total mass of protein (1.5 mg per test) based on the stated protein content of TISSEEL®. Adherends were overlapped with an area of 1.2 cm×1.2 cm and were cured for 24 h at 37° C. Bond strengths were quantified using an INSTRON®5544 Materials Testing System (Norwood, MA) with a 2000 N load cell and a loading rate of 2 mm/min. Maximum force was divided by overlap area to determine the adhesion strength. Each condition was tested with at least 5 samples.

For humid curing, adherends were covered with a layer of damp paper towels followed by a layer of plastic wrap to prevent them from drying. For underwater curing, protein solution (either $ELY_{16}$ or $mELY_{16}$) was adjusted to pH 7.5. Aluminum adherends were placed in a PBS bath at 37° C. Protein solution (10 μL) was applied to one adherend, and the other adherend was overlapped as before. For underwater testing, at least 7 samples were tested for each group.

Statistical Analysis: Data are represented as the mean±the standard deviation. All data were first examined for outliers using Grubbs' test; any outliers were discarded from further analysis. Next, Levene's test was used to assess equality of variances, and data were analyzed with one-way analysis of variance (ANOVA) followed by Tukey's Honestly Significant Difference (HSD) or the Games-Howell (for unequal variances) post hoc test. Finally, the normality of the ANOVA residuals was assessed with the Kolmogorov-Smirnov test. If the residuals were not normally distributed, the original data were transformed with the Box-Cox method, and the analysis was repeated on the transformed data. If only two groups were being compared, an unpaired t-test was used instead of ANOVA to assess statistical difference. All statistical analyses were performed with GRAPHPAD™ online software (La Jolla, CA) or Minitab 17 (State College, PA). A p-value≤0.05 was considered significant.

As shown in FIG. 1, changes occur in the mass of YKV hydrogels after swelling across a range of pH (square marker) and absolute zeta potential of YKV solution across a range of pH (circle marker). YKV was crosslinked into hydrogels using THP. Zeta potential is a measure of overall surface charge of a protein. Actually, a change in mass less than 100% indicates a shrinking. The hydrogels tended to shrink at pH where the overall charge (zeta potential) was low. Shrinking near physiological pH is useful for surgical adhesives, as it reduces the risk of pressure on nearby tissues, blood vessels, and nerves.

Figure 2:
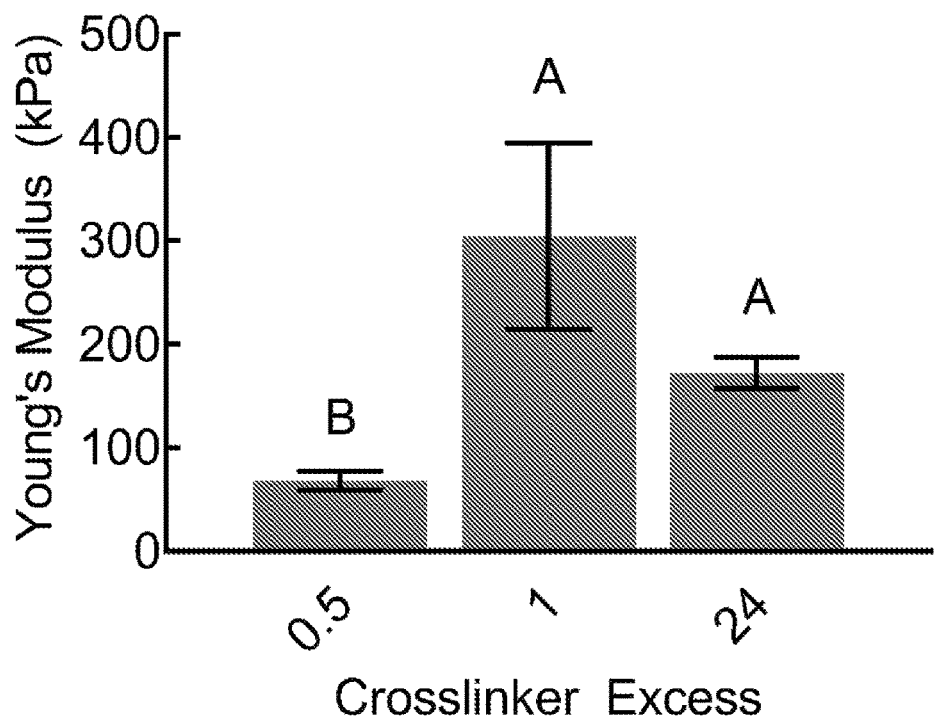
FIG. 2 shows Young's modulus (stiffness) of YKV hydrogels at varying THP crosslinker amounts swelled at pH 7. Crosslinker excess indicates the molar amount of hydroxyl groups in THP compared to the molar amount of amines in YKV. The amount of THP incorporated into a YKV hydrogel will affect the stiffness of the gel. A very high (24) or low (0.5) excess of THP will create a less connected hydrogel network, resulting in a softer gel. An equimolar amount of THP hydroxyl groups and YKV amine groups (1) creates a more highly connected network, with higher stiffness.

FIG. 2 shows Young's modulus (stiffness) of YKV hydrogels at varying THP crosslinker amounts swelled at pH 7. Crosslinker excess indicates the molar amount of hydroxyl groups in THP compared to the molar amount of amines in YKV. The amount of THP incorporated into a YKV hydrogel will affect the stiffness of the gel. A very high (24) or low (0.5) excess of THP will create a less connected hydrogel network, resulting in a softer gel. An equimolar amount of THP hydroxyl groups and YKV amine groups (1) creates a more highly connected network, with higher stiffness.

Figure 3A:
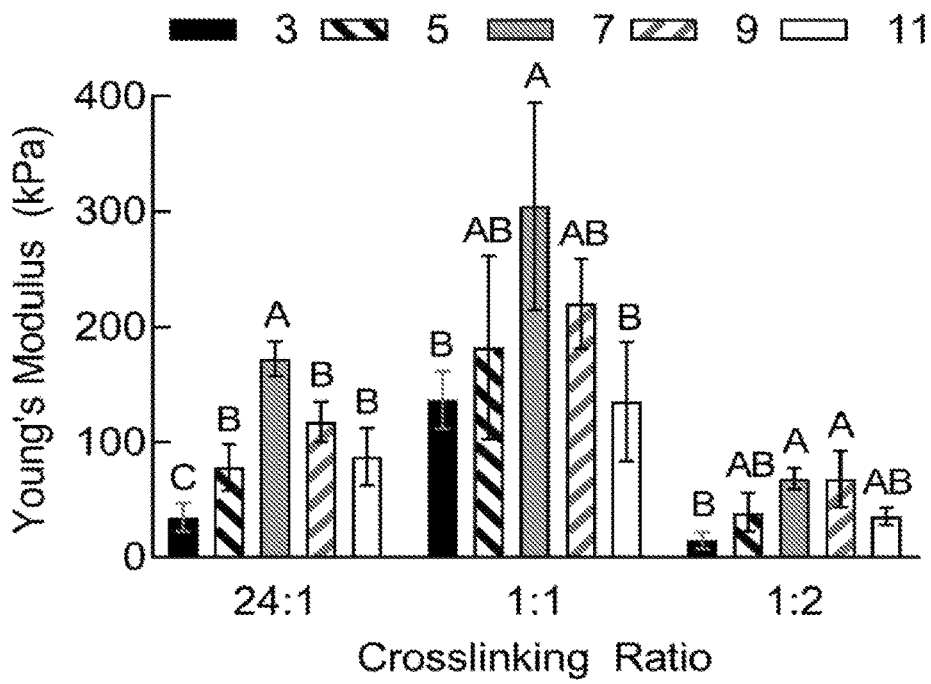
FIG. 3A shows Young's Modulus of YKV hydrogels at varying THP crosslinking ratios swelled across a range of pH. At all crosslinking ratios, YKV hydrogels tended to become stiffest near physiological pH. Changing the THP crosslinking ratio affected the amount of pH response in the hydrogels.

FIG. 3A shows Young's Modulus of YKV hydrogels at varying THP crosslinking ratios swelled across a range of pH. At all crosslinking ratios, YKV hydrogels tended to become stiffest near physiological pH. Changing the THP crosslinking ratio affected the amount of pH response in the hydrogels.

Figure 3B:
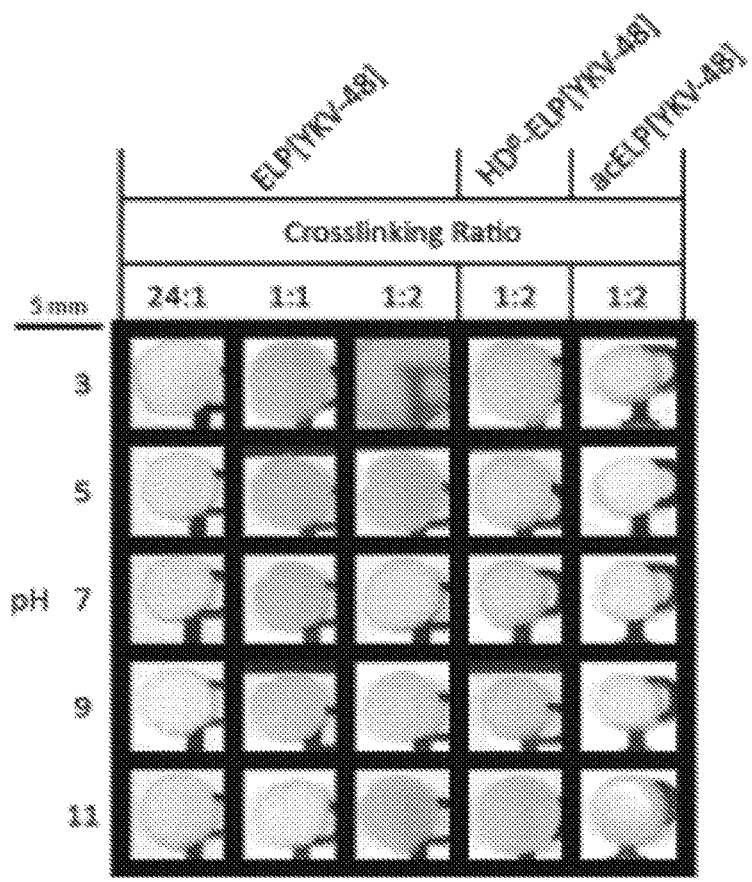
FIG. 3B shows swelling and opacity of hydrogels was affected by crosslinking ratio and acetylation. ELP[YKV-48]hydrogels with 24:1, 1:1, and 1:2 crosslinking ratio, and HD0-ELP[YKV-48] and acELP[YKV-48]hydrogels with 1:2 crosslinking ratio, swelled at pH 3 to 11 for six days. Scale bar is 5 mm.

FIG. 3B shows swelling and opacity of hydrogels was affected by crosslinking ratio and acetylation. ELP[YKV-48](SEQ ID NO: 2) hydrogels with 24:1, 1:1, and 1:2 crosslinking ratio, and HDØ-ELP[YKV-48](SEQ ID NO: 8) and acELP[YKV-48](SEQ ID NO: 14) hydrogels with 1:2 crosslinking ratio, swelled at pH 3 to 11 for six days. Scale bar is 5 mm.

Figure 4A:
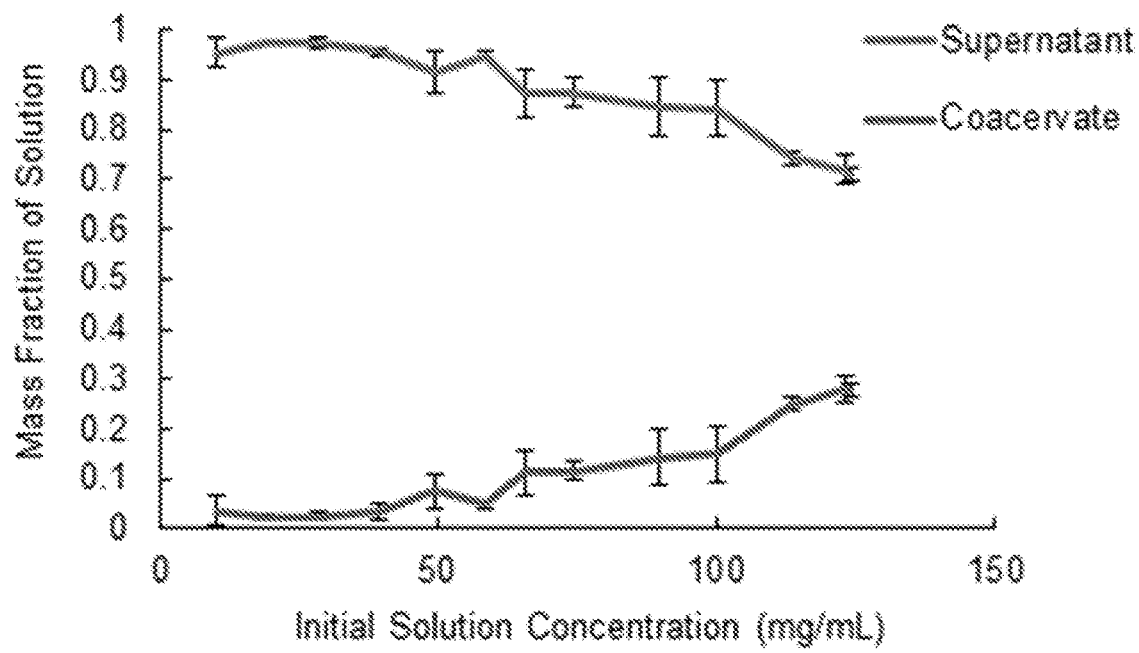
FIG. 4A describes the mass fraction of supernatant and coacervate after phase separation across a range of initial solution concentrations. As the initial solution concentration increases, the mass fraction of coacervate after phase separation increases. At ~400 mg/mL or higher, the coacervate phase has a mass fraction close to 1 (data not shown).
Figure 4B:
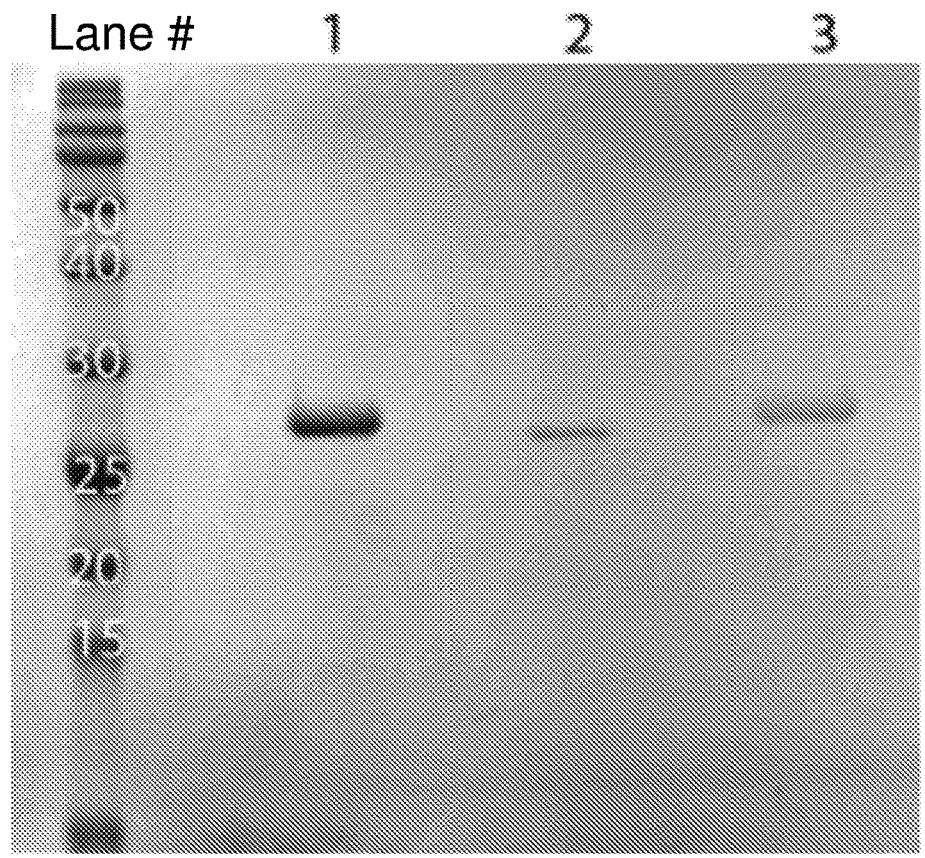
FIG. 4B depicts SDS PAGE gel of purified ELP[YKV-48](Lane #1), HD0-ELP[YKV-48](Lane #2), and acELP [YKV-48](Lane #3).

FIG. 4A describes the mass fraction of supernatant and coacervate after phase separation across a range of initial solution concentrations. As the initial solution concentration increases, the mass fraction of coacervate after phase separation increases. At ~400 mg/mL or higher, the coacervate phase has a mass fraction close to 1.

FIG. 4B depicts SDS PAGE gel of purified ELP[YKV-48](SEQ ID NO: 2) (Lane #1), HDØ-ELP[YKV-48](SEQ ID NO: 8) (Lane #2), and acELP[YKV-48](SEQ ID NO: 14) (Lane #3).

Figure 5:
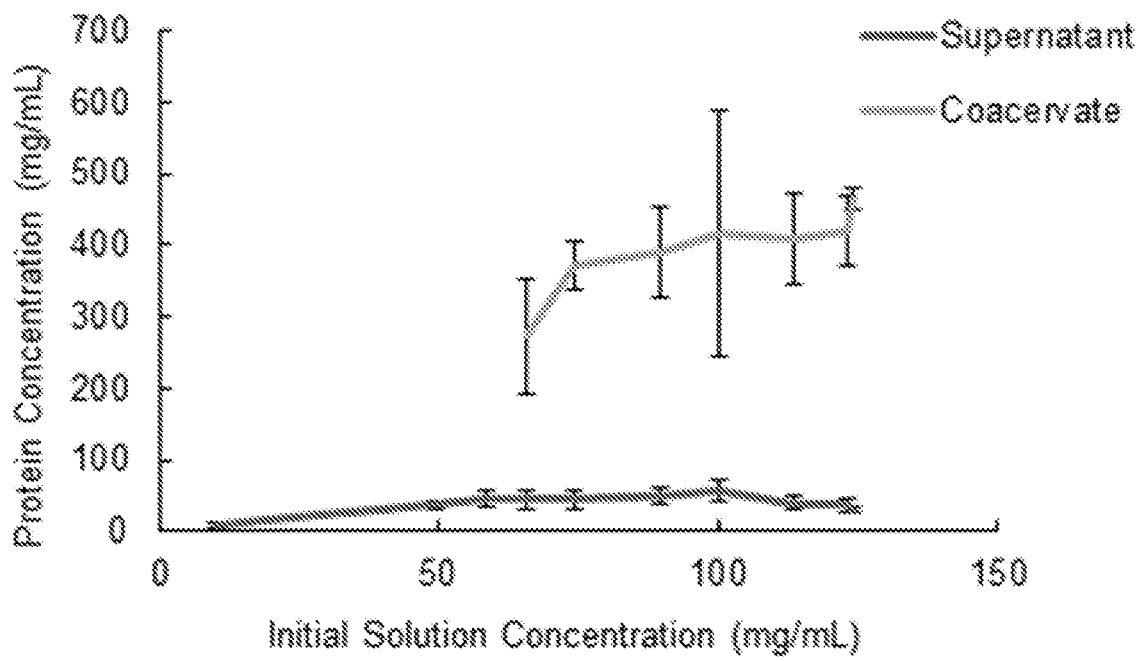
FIG. 5 shows the concentrations of supernatant and coacervate after phase separation across a range of initial solution concentrations. As initial solution concentration increases, the concentration of the supernatant plateaus. The coacervate concentration has more variability due to measuring error, but also seems to plateau.

FIG. 5 shows the concentrations of supernatant and coacervate after phase separation across a range of initial solution concentrations. As initial solution concentration increases, the concentration of the supernatant plateaus. The coacervate concentration has more variability due to measuring error, but also seems to plateau.

Figure 6:
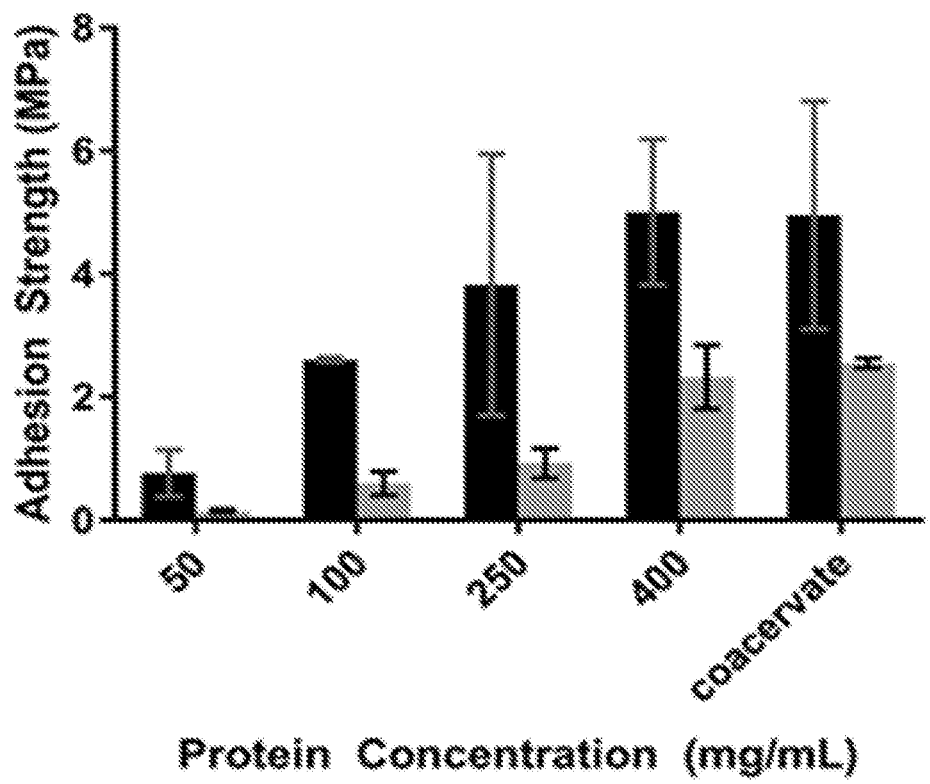
FIG. 6 depicts adhesive strength of YKV dissolved in water (black) and PBS (light grey), applied to aluminum and cured at 37° C. for 24 hours under dry conditions. Increasing protein concentration increases the adhesive strength. Using water as the solvent increases the adhesive strength compared to PBS. Isolated coacervate has similar adhesive strength to high concentration protein solutions. n=3 for water and 4 for PBS. No statistical analysis.

FIG. 6 depicts adhesive strength of YKV dissolved in water (black) and PBS (light grey), applied to aluminum and cured at 37° C. for 24 hours under dry conditions. Increasing protein concentration increases the adhesive strength. Using water as the solvent increases the adhesive strength compared to PBS. Isolated coacervate has similar adhesive strength to high concentration protein solutions. n=3 for water and 4 for PBS. No statistical analysis.

Figure 7:
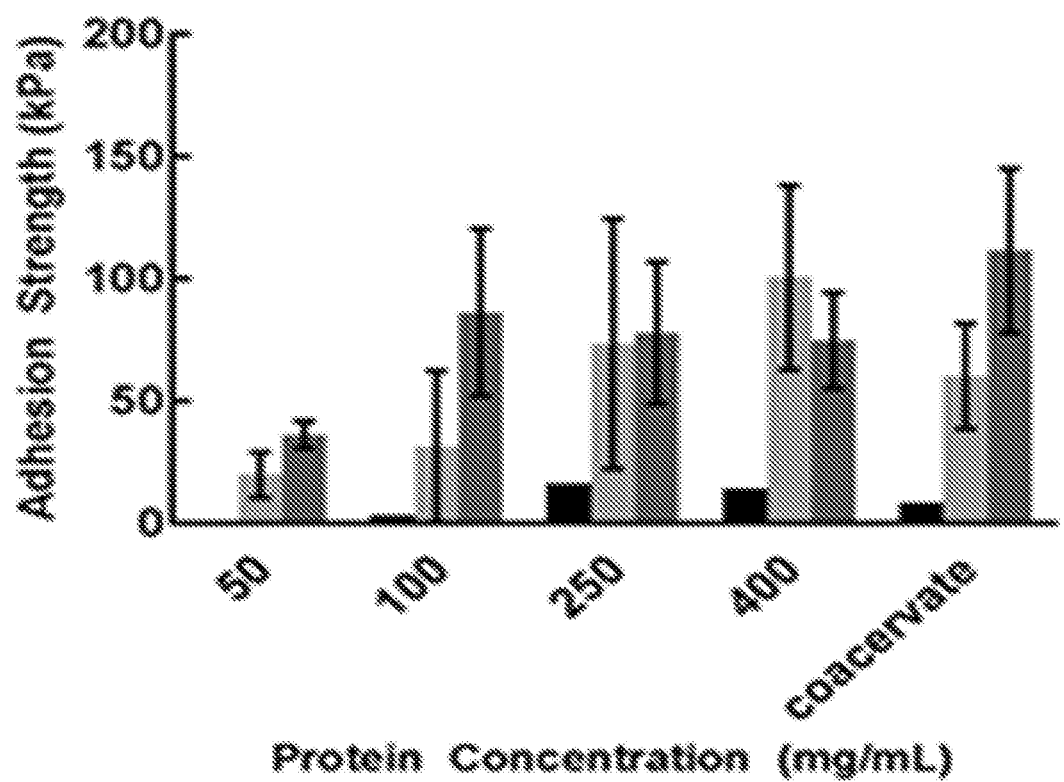
FIG. 7 shows adhesive strength of YKV dissolved in water (black) and PBS (light grey) and mYKV dissolved in PBS (dark grey), applied to aluminum and cured at 37° C. for 24 hours under humid conditions. The error bars of "YKV in water" are too small to be shown. Increasing concentration improves adhesive strength. Using PBS increases adhesive strength compared to water. At lower concentrations, mYKV has a higher adhesive strength than YKV. At higher concentrations, YKV and mYKV have similar adhesive strength. Isolate coacervate has similar adhesive strength to high concentration protein solutions. No statistical analysis.

FIG. 7 shows adhesive strength of YKV dissolved in water (black) and PBS (light grey) and mYKV dissolved in PBS (dark grey), applied to aluminum and cured at 37° C. for 24 hours under humid conditions. The error bars of "YKV in water" are too small to be shown. Increasing the concentration improves adhesive strength. Using PBS increases adhesive strength compared to water. At lower concentrations, mYKV has a higher adhesive strength than YKV. At higher concentrations, YKV and mYKV have similar adhesive strength. Isolate coacervate has similar adhesive strength to high concentration protein solutions. No statistical analysis.

Figure 8:
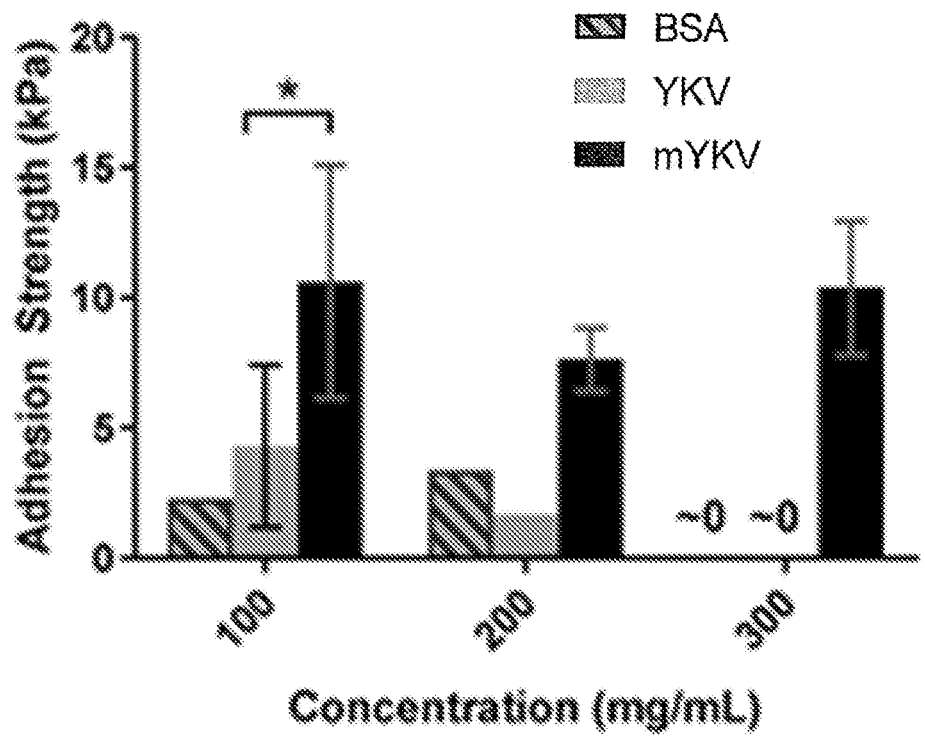
FIG. 8 demonstrates the adhesion strength of BSA (grey striped), YKV (light grey), and mYKV (black), in water at pH 7.4 on pig skin in physiological conditions (humid, 37° C.) across a range of concentrations. The addition of DOPA to YKV improves adhesion.

FIG. 8 demonstrates the adhesion strength of BSA (grey striped), YKV (light grey), and mYKV (black), in water at pH 7.4 on pig skin in physiological conditions (humid, 37° C.) across a range of concentrations. The addition of DOPA to YKV improves adhesion.

Figure 9:
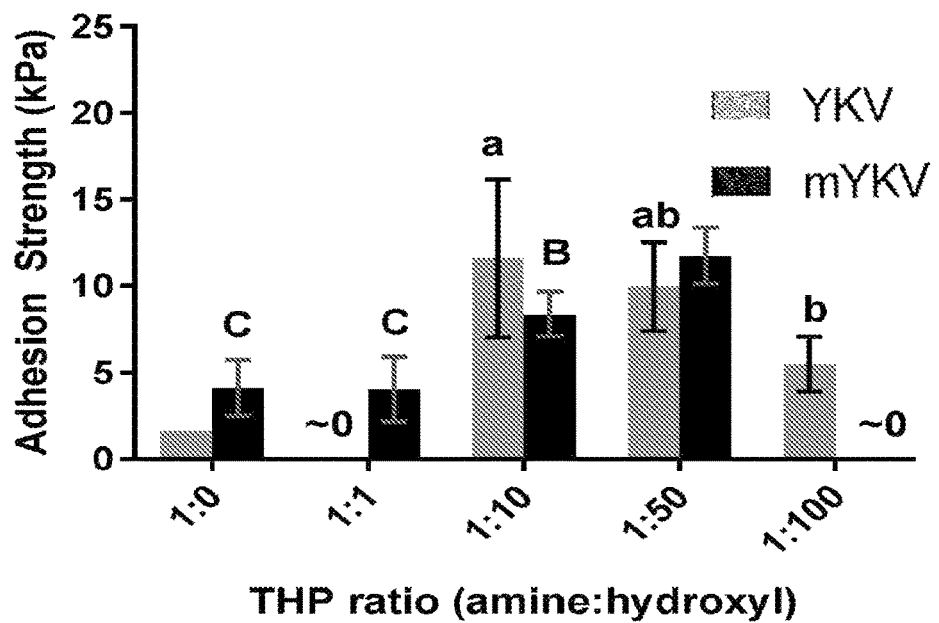
FIG. 9 shows the adhesive strength of YKV (light grey) and mYKV (black) mixed with THP at various ratios and applied to pig skin under physiological conditions (humid, 37° C.) and cured for 24 hours. 1:0 indicates protein mixed with no THP. Increasing the concentration of THP increased the adhesive strength of the protein, up to 1:50. At 1:10 and 1:50, YKV and mYKV have similar adhesive strength.

FIG. 9 shows the adhesive strength of YKV (light grey) and mYKV (black) mixed with THP at various ratios and applied to pig skin under physiological conditions (humid, 37° C.) and cured for 24 hours. 1:0 indicates protein mixed with no THP. Increasing the concentration of THP increased the adhesive strength of the protein, up to 1:50. At 1:10 and 1:50, YKV and mYKV have similar adhesive strength.

Figure 10:
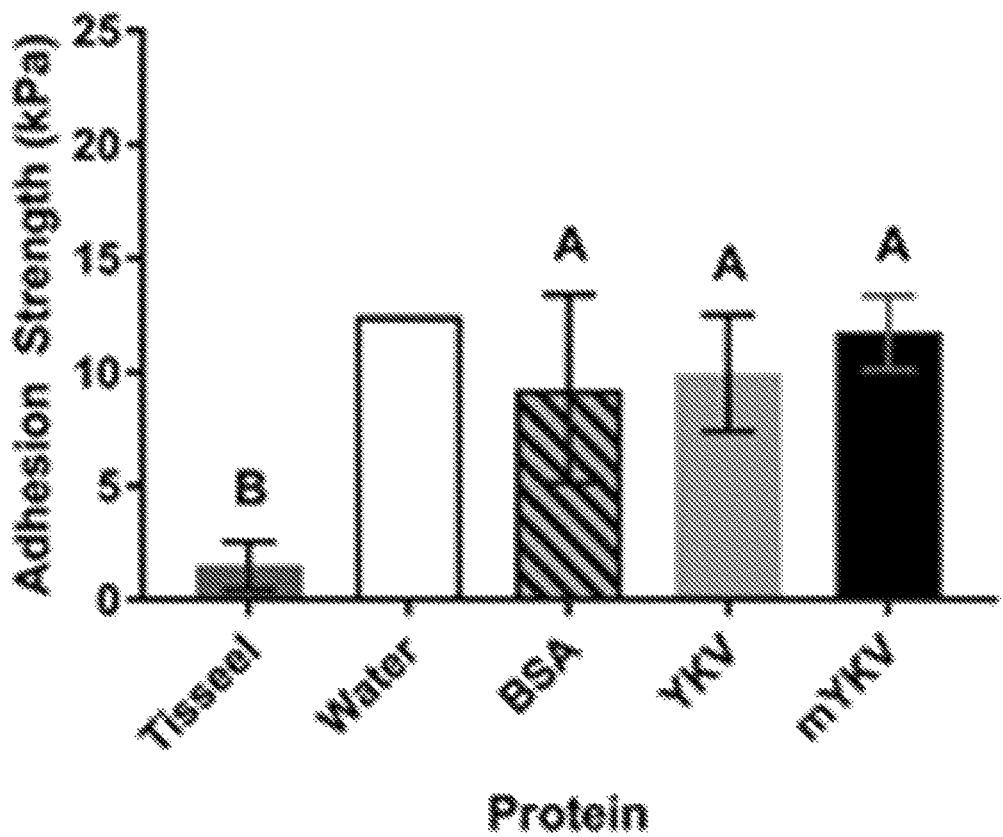
FIG. 10 describes the adhesive strength of commercial glue TISSEEL® (dark grey), and THP mixed at 1:50 with water (white), BSA (grey stripe), YKV (light grey), and mYKV (black). Various proteins mixed with THP have higher adhesion strength than TISSEEL®.

FIG. 10 describes the adhesive strength of commercial glue TISSEEL® (dark grey), and THP mixed at 1:50 with water (white), BSA (grey stripe), YKV (light grey), and mYKV (black). Various proteins mixed with THP have higher adhesion strength than TISSEEL®.

Figure 11:
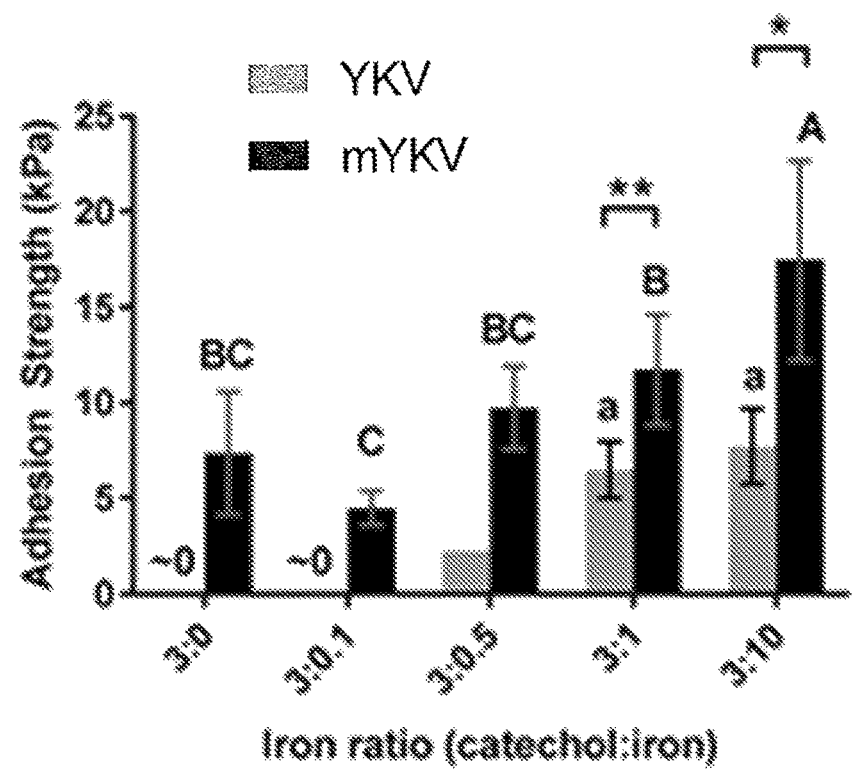
FIG. 11 shows the adhesive strength of YKV (light grey) and mYKV (black) mixed with iron nitrate nonahydrate at various ratios and applied to pig skin under physiological conditions (humid, 37° C.) and cured for 24 hours. 3:0 indicates protein mixed with no iron. Increasing the concentration of iron to a ratio of 3:10 increased the adhesive strength of the protein. At 3:1 and 3:10, mYKV had higher adhesion strength than YKV.

FIG. 11 shows the adhesive strength of YKV (light grey) and mYKV (black) mixed with iron nitrate nonahydrate at various ratios and applied to pig skin under physiological conditions (humid, 37° C.) and cured for 24 hours. 3:0 indicates protein mixed with no iron. Increasing the concentration of iron to a ratio of 3:10 increased the adhesive strength of the protein. At 3:1 and 3:10, mYKV had higher adhesion strength than YKV.

Figure 12:
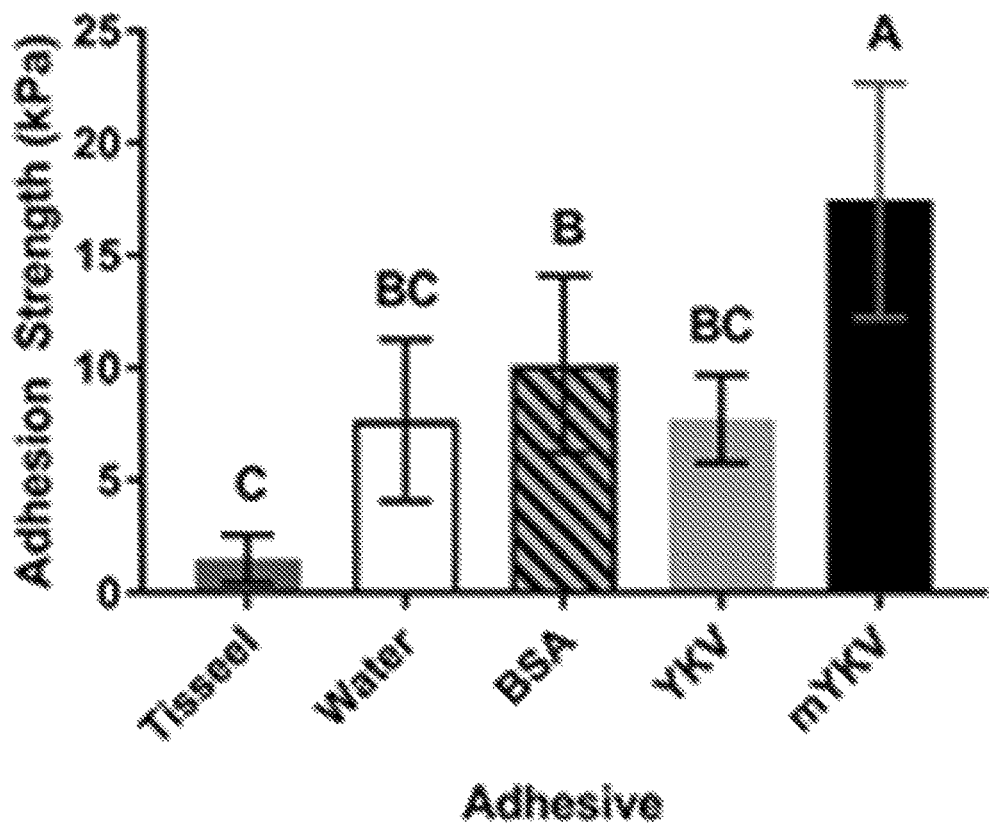
FIG. 12 describes the adhesive strength of commercial glue TISSEEL® (dark grey), and iron mixed at 3:10 with water (white), BSA (grey stripe), YKV (light grey), and mYKV (black). The addition of DOPA improves adhesion in the presence of iron. mYKV and BSA mixed with iron have higher adhesive strength than TISSEEL®.

FIG. 12 describes the adhesive strength of commercial glue TISSEEL® (dark grey), and iron mixed at 3:10 with water (white), BSA (grey stripe), YKV (light grey), and mYKV (black). The addition of DOPA improves adhesion in the presence of iron. mYKV and BSA mixed with iron have higher adhesive strength than TISSEEL®.

Figure 13:
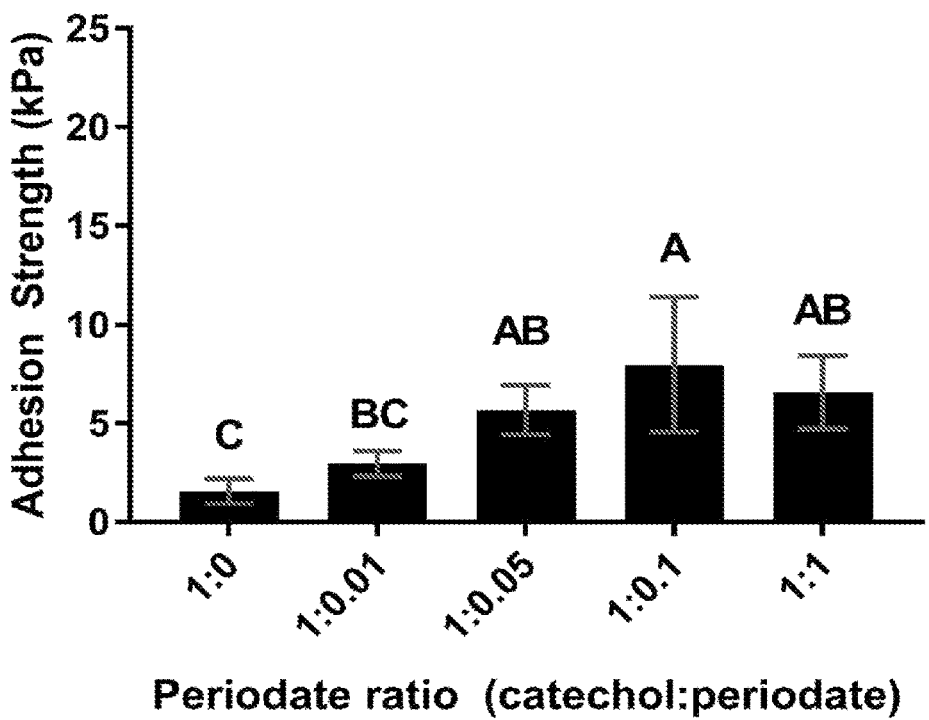
FIG. 13 shows the adhesive strength of mYKV mixed with sodium periodate at various ratios (catechol:periodate) and applied to pig skin under physiological conditions (humid, 37C) and cured for 24 hours. 1:0 indicates protein mixed with no iron. Increasing the concentration of periodate up to 1:0.1 increased the adhesive strength of the protein.

FIG. 13 shows the adhesive strength of mYKV mixed with sodium periodate at various ratios (catechol: periodate) and applied to pig skin under physiological conditions (humid, 37C) and cured for 24 hours. 1:0 indicates protein mixed with no iron. Increasing the concentration of periodate up to 1:0.1 increased the adhesive strength of the protein.

Figure 14:
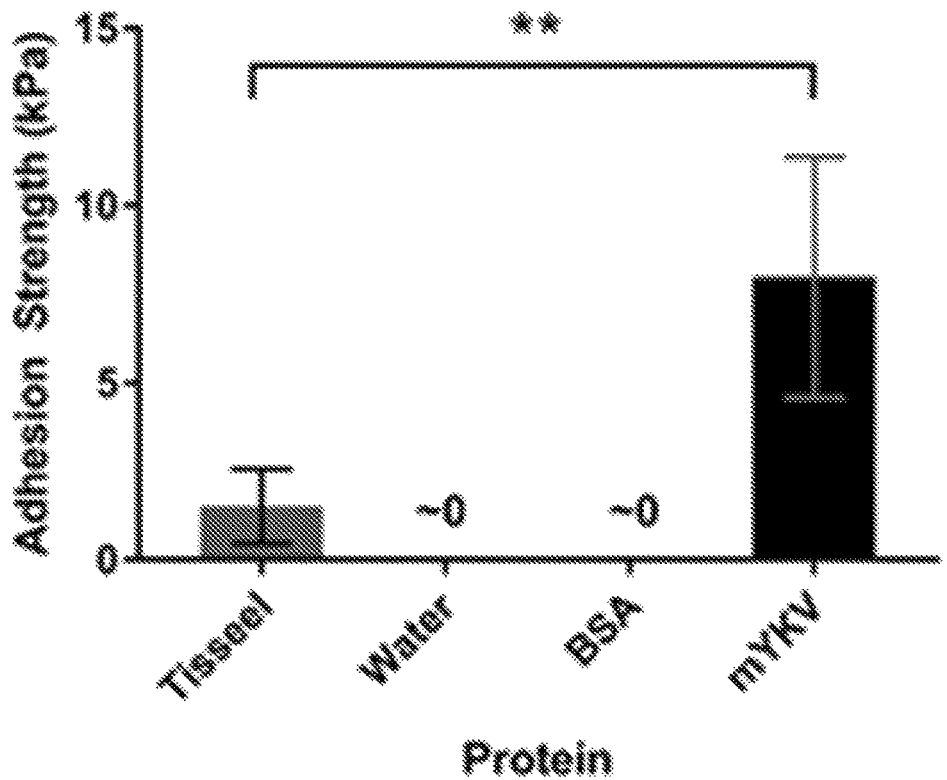
FIG. 14 shows the adhesive strength of TISSEEL® (dark grey), and periodate mixed at 1:0.1 with water (white), BSA (grey stripe), and mYKV (black). Periodate mixed with water or BSA has negligible adhesive strength. Periodate mixed with mYKV has a higher adhesive strength than TISSEEL®.

FIG. 14 shows the adhesive strength of TISSEEL® (dark grey), and periodate mixed at 1:0.1 with water (white), BSA (grey stripe), and mYKV (black). Periodate mixed with water or BSA has negligible adhesive strength. Periodate mixed with mYKV has a higher adhesive strength than TISSEEL®.

Figure 15A:
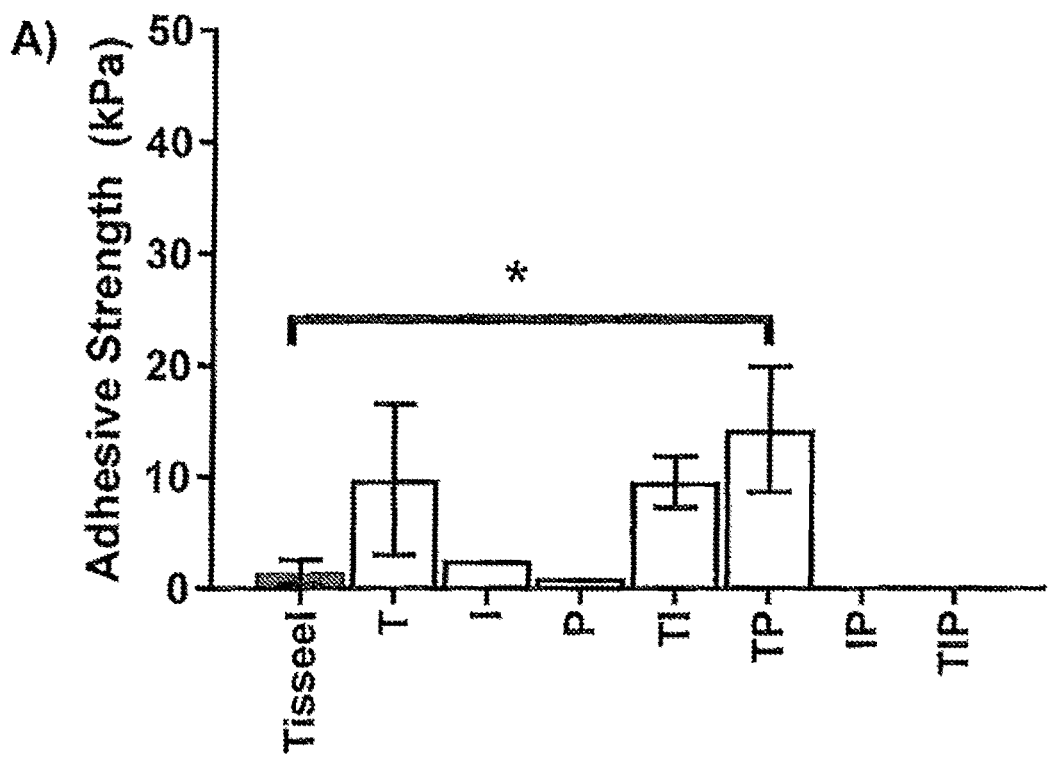
FIG. 15A shows adhesive strength of water mixed with crosslinker combinations of THP (T) at 1:50, Iron (I) at 3:10, and Periodate (P) and 1:0.1. Water mixed with TP had higher adhesion strength than TISSEEL®.

FIG. 15A shows adhesive strength of water mixed with crosslinker combinations of THP (T) at 1:50, Iron (I) at 3:10, and Periodate (P) at 1:0.1. Water mixed with TP had higher adhesion strength than TISSEEL®.

Figure 15B:
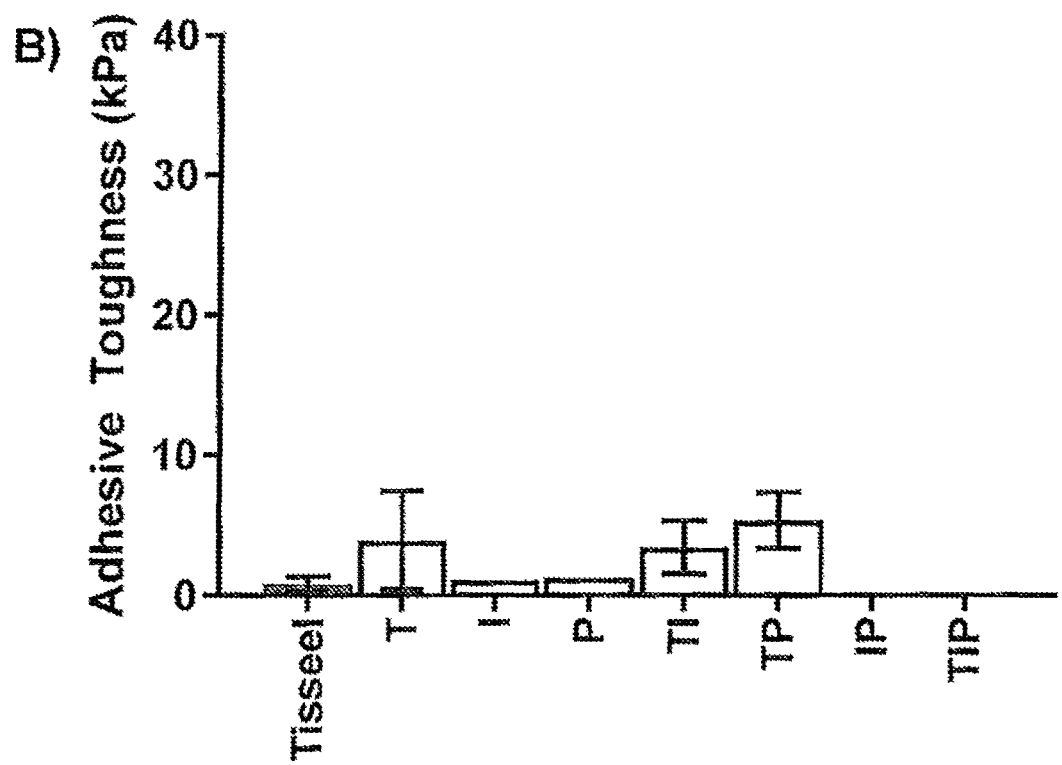
FIG. 15B shows adhesive toughness of water mixed with crosslinker combinations of THP (T) at 1:50, Iron (I) at 3:10, and Periodate (P) and 1:0.1. Water mixed with TP had higher adhesion strength than TISSEEL®.

FIG. 15B shows adhesive toughness of water mixed with crosslinker combinations of THP (T) at 1:50, Iron (I) at 3:10, and Periodate (P) and 1:0.1. Water mixed with TP had higher adhesion strength than TISSEEL®.

Figure 16A:
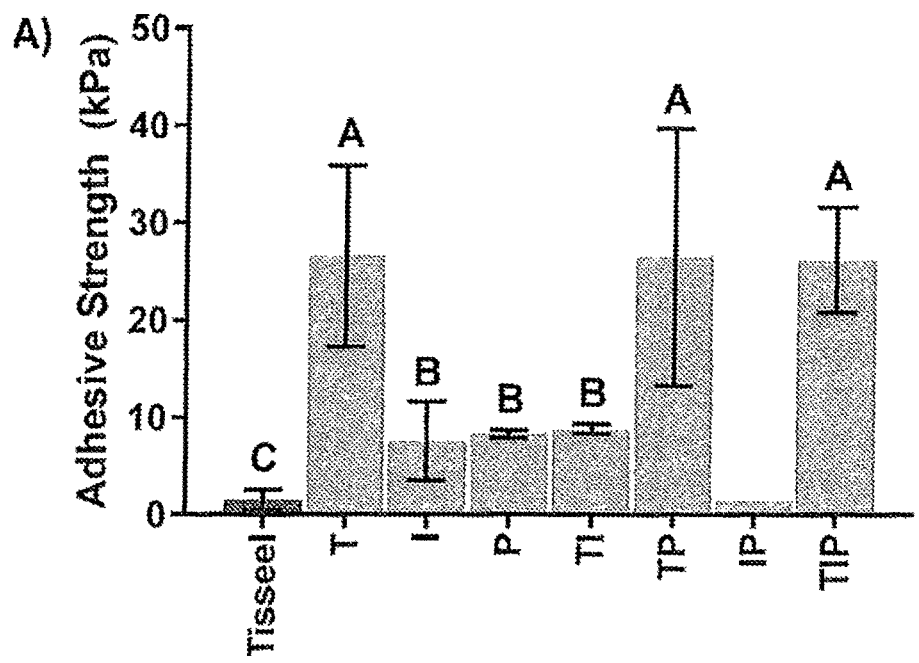
FIG. 16A shows adhesive strength of YKV mixed with crosslinker combinations of THP (T) at 1:50, Iron (I) at 3:10, and Periodate (P) and 1:0.1. YKV mixed with T, TP, and TIP had the highest adhesive strength and toughness. YKV with T, TP, and TIP had 17× higher adhesion strength than TISSEEL®.

FIG. 16A shows adhesive strength of YKV mixed with crosslinker combinations of THP (T) at 1:50, Iron (I) at 3:10, and Periodate (P) and 1:0.1. YKV mixed with T, TP, and TIP had the highest adhesive strength and toughness. YKV with T, TP, and TIP had 17× higher adhesion strength than TISSEEL®.

Figure 16B:
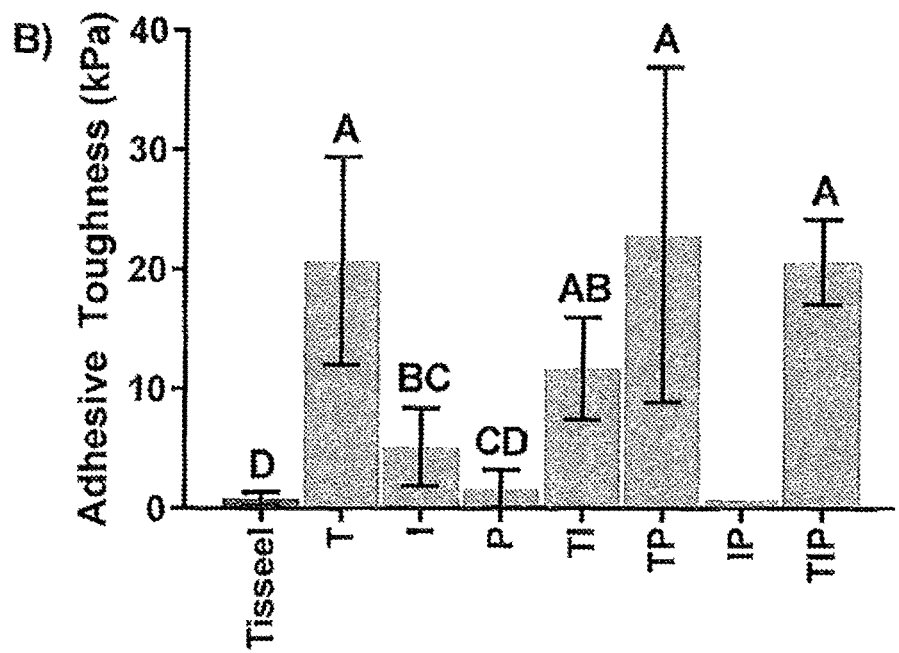
FIG. 16B depicts toughness of YKV mixed with crosslinker combinations of THP (T) at 1:50, Iron (I) at 3:10, and Periodate (P) and 1:0.1. YKV mixed with T, TP, and TIP had the highest adhesive strength and toughness. YKV with T, TP, and TIP had 17×higher adhesion strength than TISSEEL®.

FIG. 16B depicts toughness of YKV mixed with crosslinker combinations of THP (T) at 1:50, Iron (I) at 3:10, and Periodate (P) and 1:0.1. YKV mixed with T, TP, and TIP had the highest adhesive strength and toughness. YKV with T, TP, and TIP had 17× higher adhesion strength than TISSEEL®.

Figure 17A:
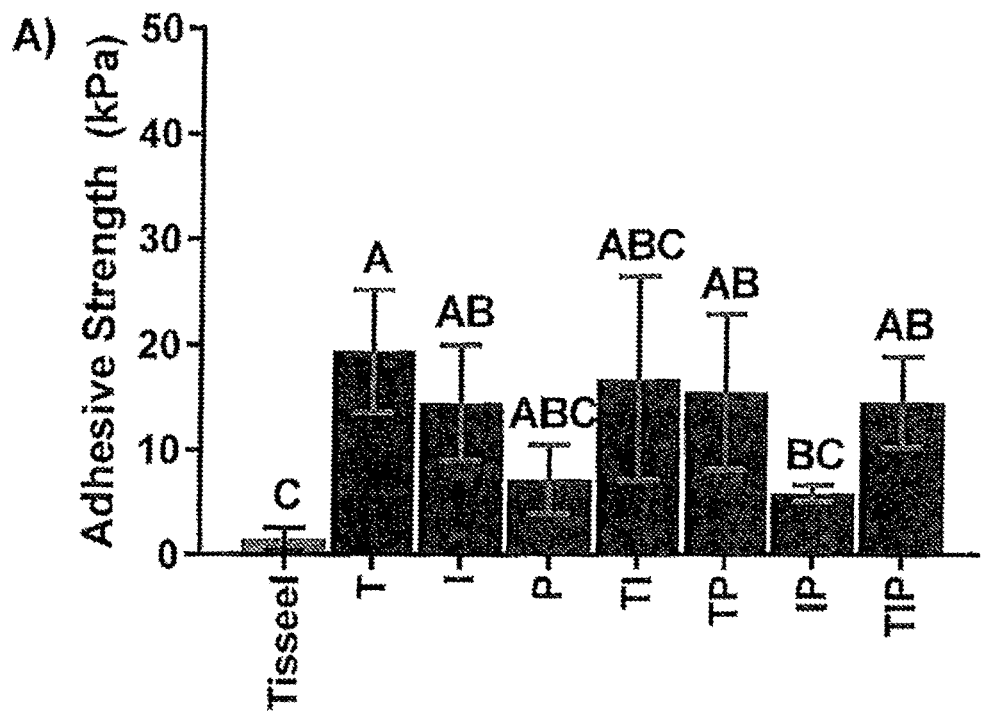
FIG. 17A shows adhesive strength of mYKV mixed with crosslinker combinations of THP (T) at 1:50, Iron (I) at 3:10, and Periodate (P) and 1:0.1. Adhesion strength was higher than TISSEEL® with T, I, TP, and TIP. Toughness was higher than TISSEEL® with I, TI, and TP.

FIG. 17A shows adhesive strength of mYKV mixed with crosslinker combinations of THP (T) at 1:50, Iron (I) at 3:10, and Periodate (P) and 1:0.1. Adhesion strength was higher than TISSEEL® with T, I, TP, and TIP. Toughness was higher than TISSEEL® with I, TI, and TP.

Figure 17B:
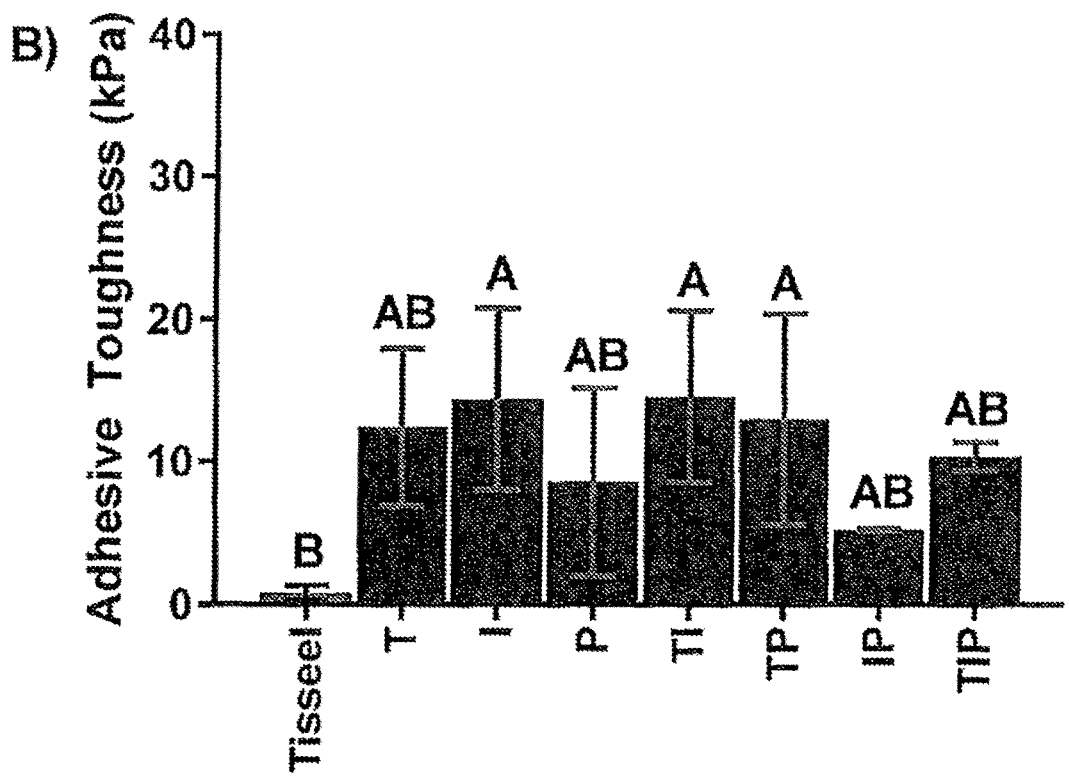
FIG. 17B shows toughness of mYKV mixed with crosslinker combinations of THP (T) at 1:50, Iron (I) at 3:10, and Periodate (P) and 1:0.1. Adhesion strength was higher than TISSEEL® with T, I, TP, and TIP. Toughness was higher than TISSEEL® with I, TI, and TP.

FIG. 17B shows toughness of mYKV mixed with crosslinker combinations of THP (T) at 1:50, Iron (I) at 3:10, and Periodate (P) and 1:0.1. Adhesion strength was higher than TISSEEL® with T, I, TP, and TIP. Toughness was higher than TISSEEL® with I, TI, and TP.

Figure 18A:
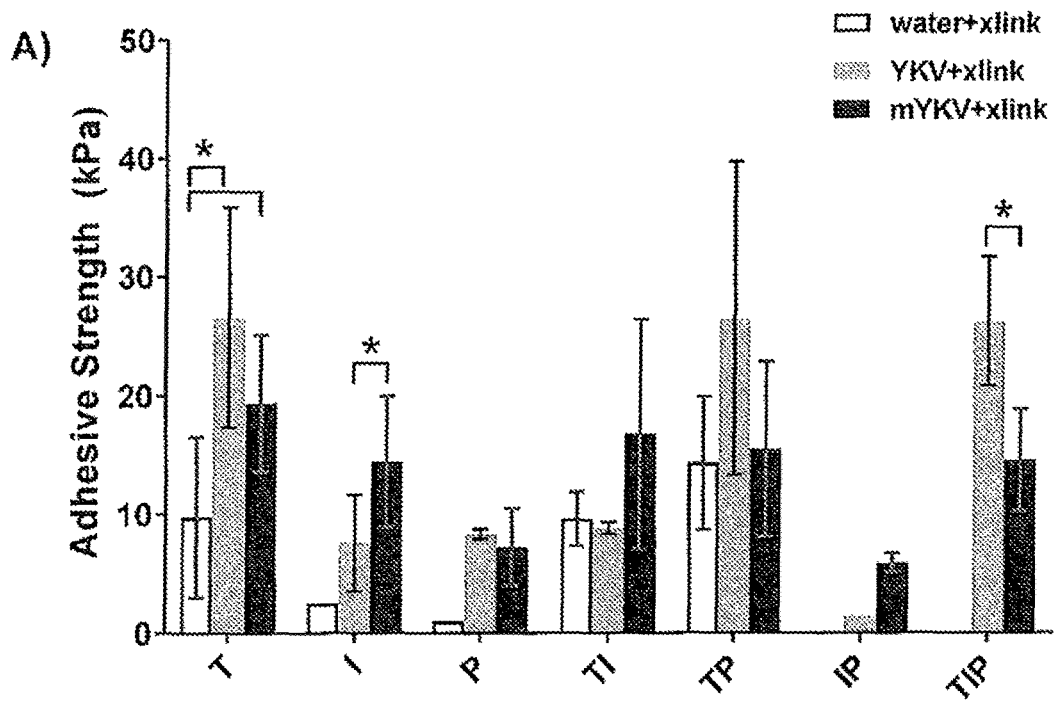
FIG. 18A depicts adhesive strength of water, YKV and mYKV mixed with crosslinker combinations of THP (T) at 1:50, Iron (I) at 3:10, and Periodate (P) and 1:0.1. YKV and mYKV had higher adhesion strength than water when mixed with T. YKV had higher adhesion strength and toughness than YKV when mixed with I. YKV had higher adhesion strength and toughness than mYKV when mixed with TIP.

FIG. 18A depicts adhesive strength of water, YKV and mYKV mixed with crosslinker combinations of THP (T) at 1:50, Iron (I) at 3:10, and Periodate (P) and 1:0.1. YKV and mYKV had higher adhesion strength than water when mixed with T. YKV had higher adhesion strength and toughness than YKV when mixed with I. YKV had higher adhesion strength and toughness than mYKV when mixed with TIP.

Figure 18B:
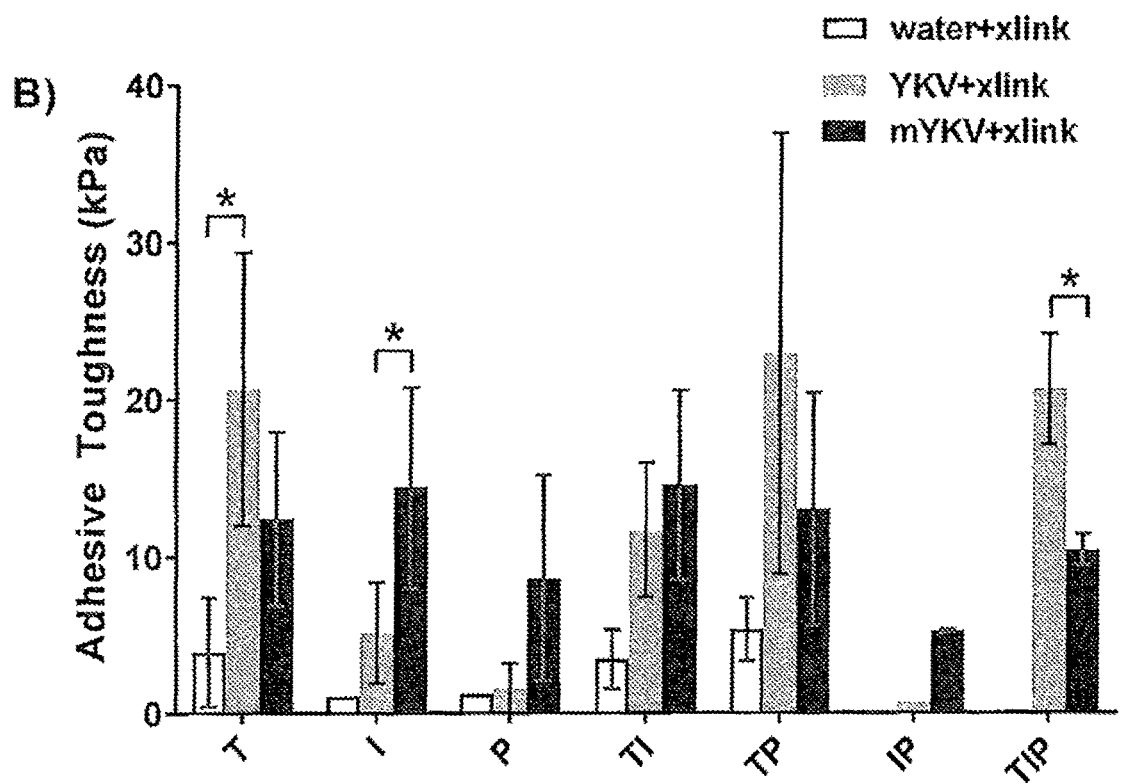
FIG. 18B shows toughness of water, YKV and mYKV mixed with crosslinker combinations of THP (T) at 1:50, Iron (I) at 3:10, and Periodate (P) and 1:0.1. YKV and mYKV had higher adhesion strength than water when mixed with T. YKV had higher adhesion strength and toughness than YKV when mixed with I. YKV had higher adhesion strength and toughness than mYKV when mixed with TIP.

FIG. 18B shows toughness of water, YKV and mYKV mixed with crosslinker combinations of THP (T) at 1:50, Iron (I) at 3:10, and Periodate (P) and 1:0.1. YKV and mYKV had higher adhesion strength than water when mixed with T. YKV had higher adhesion strength and toughness than YKV when mixed with I. YKV had higher adhesion strength and toughness than mYKV when mixed with TIP.

While various embodiments of protein-based adhesives and methods of producing the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The invention claimed is:

1. An adhesive comprising (i) a crosslinking agent selected from tetrakis(hydroxymethyl)phosphonium chloride (THPC), an N-hydroxysuccinyl ester (NHS), genipin, pyridyl disulfide, a maleimide, a vinylsulfone, a haloacetyl, and a combination thereof, (ii) an elastin-like polypeptide (ELP), wherein polypeptide chain of said ELP comprises (a) a tyrosine residue, a derivative thereof, or a combination thereof and (b) at least one of a lysine residue, a cysteine residue, or a combination thereof, and (iii) an oxidizing agent selected from a ferric salt, a hydrogen peroxide, and a sodium periodate, wherein the ELP comprises at least one of SEQ ID NOs: 4, 6, 8 or 10.

2. The adhesive of claim 1, wherein the derivative of the tyrosine residue is dihydroxyphenylalanine (DOPA), trihydroxyphenylalanine (TOPA), or a combination thereof.

3. A method of generating an adhesive comprising the steps of:
providing a crosslinking agent selected from tetrakis (hydroxymethyl)phosphonium chloride (THPC), an N-hydroxysuccinyl ester (NHS), genipin, pyridyl disulfide, a maleimide, a vinylsulfone, a haloacetyl, and a combination thereof;
adding an elastin-like polypeptide (ELP), wherein the polypeptide chain of said ELP comprises (a) a tyrosine residue, a derivative thereof, or a combination thereof and (b) at least one of a lysine residue, a cysteine residue, or a combination thereof; and
adding an oxidizing agent selected from a ferric salt, a hydrogen peroxide, and a sodium periodate, wherein the ELP comprises at least one of SEQ ID NOs: 4, 6, 8 or 10.

4. The method according to claim 3, wherein the derivative of the tyrosine residue is dihydroxyphenylalanine (DOPA), trihydroxyphenylalanine (TOPA), or a combination thereof.

* * * * *

SEQUENCE LISTING

```
<160> NUMBER OF SEQ ID NOS: 14

<210> SEQ ID NO 1
<211> LENGTH: 837
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(837)

<400> SEQUENCE: 1 atg atg gct agc atg act ggt gga cag caa atg ggt cac cac cac cac      48
Met Met Ala Ser Met Thr Gly Gly Gln Gln Met Gly His His His His
1               5                   10                  15 cac cac cat gat gat gat gat aaa ctc gac ggg acc ctc ccg ggc tat      96
His His His Asp Asp Asp Asp Lys Leu Asp Gly Thr Leu Pro Gly Tyr
            20                  25                  30 ggg gtg ccg ggt aaa ggc gtt ccg ggt gtg ggc gta ccg ggt tac ggc     144
Gly Val Pro Gly Lys Gly Val Pro Gly Val Gly Val Pro Gly Tyr Gly
        35                  40                  45
```

| | | |
|---|---|---|
| gta ccg ggt aaa ggg gtt cca ggc gtg ggt gta ccg ggc tat ggg gtg<br>Val Pro Gly Lys Gly Val Pro Gly Val Gly Val Pro Gly Tyr Gly Val<br>50                       55                    60 | | 192 |
| ccg ggt aaa ggc gtt ccg ggt gtg ggc gta ccg ggt tac ggc gta ccg<br>Pro Gly Lys Gly Val Pro Gly Val Gly Val Pro Gly Tyr Gly Val Pro<br>65                       70                    75                    80 | | 240 |
| ggt aaa ggg gtt cca ggc gtg ggt gta ccg ggc tat ggg gtg ccg ggt<br>Gly Lys Gly Val Pro Gly Val Gly Val Pro Gly Tyr Gly Val Pro Gly<br>              85                    90                    95 | | 288 |
| aaa ggc gtt ccg ggt gtg ggc gta ccg ggt tac ggc gta ccg ggt aaa<br>Lys Gly Val Pro Gly Val Gly Val Pro Gly Tyr Gly Val Pro Gly Lys<br>              100                  105                  110 | | 336 |
| ggg gtt cca ggc gtg ggt gta ccg ggc tat ggg gtg ccg ggt aaa ggc<br>Gly Val Pro Gly Val Gly Val Pro Gly Tyr Gly Val Pro Gly Lys Gly<br>        115                  120                  125 | | 384 |
| gtt ccg ggt gtg ggc gta ccg ggt tac ggc gta ccg ggt aaa ggg gtt<br>Val Pro Gly Val Gly Val Pro Gly Tyr Gly Val Pro Gly Lys Gly Val<br>130                      135                  140 | | 432 |
| cca ggc gtg ggt gta ccg ggc tat ggg gtg ccg ggt aaa ggc gtt ccg<br>Pro Gly Val Gly Val Pro Gly Tyr Gly Val Pro Gly Lys Gly Val Pro<br>145                      150                  155                  160 | | 480 |
| ggt gtg ggc gta ccg ggt tac ggc gta ccg ggt aaa ggg gtt cca ggc<br>Gly Val Gly Val Pro Gly Tyr Gly Val Pro Gly Lys Gly Val Pro Gly<br>              165                  170                  175 | | 528 |
| gtg ggt gta ccg ggc tat ggg gtg ccg ggt aaa ggc gtt ccg ggt gtg<br>Val Gly Val Pro Gly Tyr Gly Val Pro Gly Lys Gly Val Pro Gly Val<br>              180                  185                  190 | | 576 |
| ggc gta ccg ggt tac ggc gta ccg ggt aaa ggg gtt cca ggc gtg ggt<br>Gly Val Pro Gly Tyr Gly Val Pro Gly Lys Gly Val Pro Gly Val Gly<br>              195                  200                  205 | | 624 |
| gta ccg ggc tat ggg gtg ccg ggt aaa ggc gtt ccg ggt gtg ggc gta<br>Val Pro Gly Tyr Gly Val Pro Gly Lys Gly Val Pro Gly Val Gly Val<br>        210                  215                  220 | | 672 |
| ccg ggt tac ggc gta ccg ggt aaa ggg gtt ccg ggt gtg ggc gta ccg<br>Pro Gly Tyr Gly Val Pro Gly Lys Gly Val Pro Gly Val Gly Val Pro<br>225                      230                  235                  240 | | 720 |
| ggc tat ggg gtg ccg ggt aaa ggc gtt ccg ggt gtg ggc gta ccg ggt<br>Gly Tyr Gly Val Pro Gly Lys Gly Val Pro Gly Val Gly Val Pro Gly<br>              245                  250                  255 | | 768 |
| tac ggc gta ccg ggt aaa ggg gtt cca ggc gtg ggt gta ccg gta gcg<br>Tyr Gly Val Pro Gly Lys Gly Val Pro Gly Val Gly Val Pro Val Ala<br>        260                  265                  270 | | 816 |
| gac cgt gga atg cgg ctc gag<br>Asp Arg Gly Met Arg Leu Glu<br>        275 | | 837 |

<210> SEQ ID NO 2
<211> LENGTH: 279
<212> TYPE: PRT
<213> ORGANISM: Artificial Sequence
<220> FEATURE:
<223> OTHER INFORMATION: Synthetic Construct

<400> SEQUENCE: 2

Met Met Ala Ser Met Thr Gly Gly Gln Gln Met Gly His His His His
1               5                   10                  15

His His His Asp Asp Asp Lys Leu Asp Gly Thr Leu Pro Gly Tyr
            20                  25                  30

Gly Val Pro Gly Lys Gly Val Pro Gly Val Gly Val Pro Gly Tyr Gly
        35                  40                  45

```
Val Pro Gly Lys Gly Val Pro Gly Val Gly Val Pro Gly Tyr Gly Val
     50                  55                  60

Pro Gly Lys Gly Val Pro Gly Val Gly Val Pro Gly Tyr Gly Val Pro
 65                  70                  75                  80

Gly Lys Gly Val Pro Gly Val Gly Val Pro Gly Tyr Gly Val Pro Gly
                 85                  90                  95

Lys Gly Val Pro Gly Val Gly Val Pro Gly Tyr Gly Val Pro Gly Lys
            100                 105                 110

Gly Val Pro Gly Val Gly Val Pro Gly Tyr Gly Val Pro Gly Lys Gly
        115                 120                 125

Val Pro Gly Val Gly Val Pro Gly Tyr Gly Val Pro Gly Lys Gly Val
    130                 135                 140

Pro Gly Val Gly Val Pro Gly Tyr Gly Val Pro Gly Lys Gly Val Pro
145                 150                 155                 160

Gly Val Gly Val Pro Gly Tyr Gly Val Pro Gly Lys Gly Val Pro Gly
                165                 170                 175

Val Gly Val Pro Gly Tyr Gly Val Pro Gly Lys Gly Val Pro Gly Val
            180                 185                 190

Gly Val Pro Gly Tyr Gly Val Pro Gly Lys Gly Val Pro Gly Val Gly
        195                 200                 205

Val Pro Gly Tyr Gly Val Pro Gly Lys Gly Val Pro Gly Val Gly Val
    210                 215                 220

Pro Gly Tyr Gly Val Pro Gly Lys Gly Val Pro Gly Val Gly Val Pro
225                 230                 235                 240

Gly Tyr Gly Val Pro Gly Lys Gly Val Pro Gly Val Gly Val Pro Gly
                245                 250                 255

Tyr Gly Val Pro Gly Lys Gly Val Pro Gly Val Gly Val Pro Val Ala
            260                 265                 270

Asp Arg Gly Met Arg Leu Glu
        275

<210> SEQ ID NO 3
<211> LENGTH: 1197
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1197)

<400> SEQUENCE: 3 atg atg gct agc atg act ggt gga cag caa atg ggt cac cac cac cac      48
Met Met Ala Ser Met Thr Gly Gly Gln Gln Met Gly His His His His
 1               5                  10                  15 cac cac cat gat gat gat gat aaa ctc gac ggg acc ctc ccg ggc tat      96
His His His Asp Asp Asp Asp Lys Leu Asp Gly Thr Leu Pro Gly Tyr
                20                  25                  30 ggg gtg ccg ggt aaa ggc gtt ccg ggt gtg ggc gta ccg ggt tac ggc     144
Gly Val Pro Gly Lys Gly Val Pro Gly Val Gly Val Pro Gly Tyr Gly
            35                  40                  45 gta ccg ggt aaa ggg gtt cca ggc gtg ggt gta ccg ggc tat ggg gtg     192
Val Pro Gly Lys Gly Val Pro Gly Val Gly Val Pro Gly Tyr Gly Val
        50                  55                  60 ccg ggt aaa ggc gtt ccg ggt gtg ggc gta ccg ggt tac ggc gta ccg     240
Pro Gly Lys Gly Val Pro Gly Val Gly Val Pro Gly Tyr Gly Val Pro
 65                  70                  75                  80 ggt aaa ggg gtt cca ggc gtg ggt gta ccg ggc tat ggg gtg ccg ggt     288
```

```
                Gly Lys Gly Val Pro Gly Val Gly Val Pro Gly Tyr Gly Val Pro Gly
                                85                  90                  95 aaa ggc gtt ccg ggt gtg ggc gta ccg ggt tac ggc gta ccg ggt aaa         336
Lys Gly Val Pro Gly Val Gly Val Pro Gly Tyr Gly Val Pro Gly Lys
                100                 105                 110 ggg gtt cca ggc gtg ggt gta ccg ggc tat ggg gtg ccg ggt aaa ggc         384
Gly Val Pro Gly Val Gly Val Pro Gly Tyr Gly Val Pro Gly Lys Gly
                115                 120                 125 gtt ccg ggt gtg ggc gta ccg ggt tac ggc gta ccg ggt aaa ggg gtt         432
Val Pro Gly Val Gly Val Pro Gly Tyr Gly Val Pro Gly Lys Gly Val
            130                 135                 140 cca ggc gtg ggt gta ccg ggc tat ggg gtg ccg ggt aaa ggc gtt ccg         480
Pro Gly Val Gly Val Pro Gly Tyr Gly Val Pro Gly Lys Gly Val Pro
145                 150                 155                 160 ggt gtg ggc gta ccg ggt tac ggc gta ccg ggt aaa ggg gtt cca ggc         528
Gly Val Gly Val Pro Gly Tyr Gly Val Pro Gly Lys Gly Val Pro Gly
                165                 170                 175 gtg ggt gta ccg ggc tat ggg gtg ccg ggt aaa ggc gtt ccg ggt gtg         576
Val Gly Val Pro Gly Tyr Gly Val Pro Gly Lys Gly Val Pro Gly Val
            180                 185                 190 ggc gta ccg ggt tac ggc gta ccg ggt aaa ggg gtt cca ggc gtg ggt         624
Gly Val Pro Gly Tyr Gly Val Pro Gly Lys Gly Val Pro Gly Val Gly
        195                 200                 205 gta ccg ggc tat ggg gtg ccg ggt aaa ggc gtt ccg ggt gtg ggc gta         672
Val Pro Gly Tyr Gly Val Pro Gly Lys Gly Val Pro Gly Val Gly Val
    210                 215                 220 ccg ggt tac ggc gta ccg ggt aaa ggg gtt cca ggc gtg ggt gta ccg         720
Pro Gly Tyr Gly Val Pro Gly Lys Gly Val Pro Gly Val Gly Val Pro
225                 230                 235                 240 ggc tat ggg gtg ccg ggt aaa ggc gtt ccg ggt gtg ggc gta ccg ggt         768
Gly Tyr Gly Val Pro Gly Lys Gly Val Pro Gly Val Gly Val Pro Gly
                245                 250                 255 tac ggc gta ccg ggt aaa ggg gtt cca ggc gtg ggt gta ccg ggc tat         816
Tyr Gly Val Pro Gly Lys Gly Val Pro Gly Val Gly Val Pro Gly Tyr
            260                 265                 270 ggg gtg ccg ggt aaa ggc gtt ccg ggt gtg ggc gta ccg ggt tac ggc         864
Gly Val Pro Gly Lys Gly Val Pro Gly Val Gly Val Pro Gly Tyr Gly
        275                 280                 285 gta ccg ggt aaa ggg gtt cca ggc gtg ggt gta ccg ggc tat ggg gtg         912
Val Pro Gly Lys Gly Val Pro Gly Val Gly Val Pro Gly Tyr Gly Val
    290                 295                 300 ccg ggt aaa ggc gtt ccg ggt gtg ggc gta ccg ggt tac ggc gta ccg         960
Pro Gly Lys Gly Val Pro Gly Val Gly Val Pro Gly Tyr Gly Val Pro
305                 310                 315                 320 ggt aaa ggg gtt cca ggc gtg ggt gta ccg ggc tat ggg gtg ccg ggt         1008
Gly Lys Gly Val Pro Gly Val Gly Val Pro Gly Tyr Gly Val Pro Gly
                325                 330                 335 aaa ggc gtt ccg ggt gtg ggc gta ccg ggt tac ggc gta ccg ggt aaa         1056
Lys Gly Val Pro Gly Val Gly Val Pro Gly Tyr Gly Val Pro Gly Lys
            340                 345                 350 ggg gtt cca ggc gtg ggt gta ccg ggc tat ggg gtg ccg ggt aaa ggc         1104
Gly Val Pro Gly Val Gly Val Pro Gly Tyr Gly Val Pro Gly Lys Gly
        355                 360                 365 gtt ccg ggt gtg ggc gta ccg ggt tac ggc gta ccg ggt aaa ggg gtt         1152
Val Pro Gly Val Gly Val Pro Gly Tyr Gly Val Pro Gly Lys Gly Val
    370                 375                 380 cca ggc gtg ggt gta ccg gta gcg gac cgt gga atg cgg ctc gag             1197
Pro Gly Val Gly Val Pro Val Ala Asp Arg Gly Met Arg Leu Glu
385                 390                 395
```

<210> SEQ ID NO 4
<211> LENGTH: 399
<212> TYPE: PRT
<213> ORGANISM: Artificial Sequence
<220> FEATURE:
<223> OTHER INFORMATION: Synthetic Construct

<400> SEQUENCE: 4

```
Met Met Ala Ser Met Thr Gly Gly Gln Gln Met Gly His His His His
1               5                   10                  15

His His His Asp Asp Asp Asp Lys Leu Asp Gly Thr Leu Pro Gly Tyr
                20                  25                  30

Gly Val Pro Gly Lys Gly Val Pro Gly Val Gly Val Pro Gly Tyr Gly
            35                  40                  45

Val Pro Gly Lys Gly Val Pro Gly Val Gly Val Pro Gly Tyr Gly Val
        50                  55                  60

Pro Gly Lys Gly Val Pro Gly Val Gly Val Pro Gly Tyr Gly Val Pro
65                  70                  75                  80

Gly Lys Gly Val Pro Gly Val Gly Val Pro Gly Tyr Gly Val Pro Gly
                85                  90                  95

Lys Gly Val Pro Gly Val Gly Val Pro Gly Tyr Gly Val Pro Gly Lys
            100                 105                 110

Gly Val Pro Gly Val Gly Val Pro Gly Tyr Gly Val Pro Gly Lys Gly
        115                 120                 125

Val Pro Gly Val Gly Val Pro Gly Tyr Gly Val Pro Gly Lys Gly Val
    130                 135                 140

Pro Gly Val Gly Val Pro Gly Tyr Gly Val Pro Gly Lys Gly Val Pro
145                 150                 155                 160

Gly Val Gly Val Pro Gly Tyr Gly Val Pro Gly Lys Gly Val Pro Gly
                165                 170                 175

Val Gly Val Pro Gly Tyr Gly Val Pro Gly Lys Gly Val Pro Gly Val
            180                 185                 190

Gly Val Pro Gly Tyr Gly Val Pro Gly Lys Gly Val Pro Gly Val Gly
        195                 200                 205

Val Pro Gly Tyr Gly Val Pro Gly Lys Gly Val Pro Gly Val Gly Val
    210                 215                 220

Pro Gly Tyr Gly Val Pro Gly Lys Gly Val Pro Gly Val Gly Val Pro
225                 230                 235                 240

Gly Tyr Gly Val Pro Gly Lys Gly Val Pro Gly Val Gly Val Pro Gly
                245                 250                 255

Tyr Gly Val Pro Gly Lys Gly Val Pro Gly Val Gly Val Pro Gly Tyr
            260                 265                 270

Gly Val Pro Gly Lys Gly Val Pro Gly Val Gly Val Pro Gly Tyr Gly
        275                 280                 285

Val Pro Gly Lys Gly Val Pro Gly Val Gly Val Pro Gly Tyr Gly Val
    290                 295                 300

Pro Gly Lys Gly Val Pro Gly Val Gly Val Pro Gly Tyr Gly Val Pro
305                 310                 315                 320

Gly Lys Gly Val Pro Gly Val Gly Val Pro Gly Tyr Gly Val Pro Gly
                325                 330                 335

Lys Gly Val Pro Gly Val Gly Val Pro Gly Tyr Gly Val Pro Gly Lys
            340                 345                 350

Gly Val Pro Gly Val Gly Val Pro Gly Tyr Gly Val Pro Gly Lys Gly
        355                 360                 365
```

```
Val Pro Gly Val Gly Val Pro Gly Tyr Gly Val Pro Gly Lys Gly Val
    370                 375                 380

Pro Gly Val Gly Val Pro Val Ala Asp Arg Gly Met Arg Leu Glu
385                 390                 395

<210> SEQ ID NO 5
<211> LENGTH: 1557
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1557)

<400> SEQUENCE: 5 atg atg gct agc atg act ggt gga cag caa atg ggt cac cac cac cac    48
Met Met Ala Ser Met Thr Gly Gly Gln Gln Met Gly His His His His
1               5                   10                  15 cac cac cat gat gat gat gat aaa ctc gac ggg acc ctc ccg ggc tat    96
His His His Asp Asp Asp Asp Lys Leu Asp Gly Thr Leu Pro Gly Tyr
                20                  25                  30 ggg gtg ccg ggt aaa ggc gtt ccg ggt gtg ggc gta ccg ggt tac ggc    144
Gly Val Pro Gly Lys Gly Val Pro Gly Val Gly Val Pro Gly Tyr Gly
            35                  40                  45 gta ccg ggt aaa ggg gtt cca ggc gtg ggt gta ccg ggc tat ggg gtg    192
Val Pro Gly Lys Gly Val Pro Gly Val Gly Val Pro Gly Tyr Gly Val
        50                  55                  60 ccg ggt aaa ggc gtt ccg ggt gtg ggc gta ccg ggt tac ggc gta ccg    240
Pro Gly Lys Gly Val Pro Gly Val Gly Val Pro Gly Tyr Gly Val Pro
65                  70                  75                  80 ggt aaa ggg gtt cca ggc gtg ggt gta ccg ggc tat ggg gtg ccg ggt    288
Gly Lys Gly Val Pro Gly Val Gly Val Pro Gly Tyr Gly Val Pro Gly
                85                  90                  95 aaa ggc gtt ccg ggt gtg ggc gta ccg ggt tac ggc gta ccg ggt aaa    336
Lys Gly Val Pro Gly Val Gly Val Pro Gly Tyr Gly Val Pro Gly Lys
            100                 105                 110 ggg gtt cca ggc gtg ggt gta ccg ggc tat ggg gtg ccg ggt aaa ggc    384
Gly Val Pro Gly Val Gly Val Pro Gly Tyr Gly Val Pro Gly Lys Gly
        115                 120                 125 gtt ccg ggt gtg ggc gta ccg ggt tac ggc gta ccg ggt aaa ggg gtt    432
Val Pro Gly Val Gly Val Pro Gly Tyr Gly Val Pro Gly Lys Gly Val
    130                 135                 140 cca ggc gtg ggt gta ccg ggc tat ggg gtg ccg ggt aaa ggc gtt ccg    480
Pro Gly Val Gly Val Pro Gly Tyr Gly Val Pro Gly Lys Gly Val Pro
145                 150                 155                 160 ggt gtg ggc gta ccg ggt tac ggc gta ccg ggt aaa ggg gtt cca ggc    528
Gly Val Gly Val Pro Gly Tyr Gly Val Pro Gly Lys Gly Val Pro Gly
                165                 170                 175 gtg ggt gta ccg ggc tat ggg gtg ccg ggt aaa ggc gtt ccg ggt gtg    576
Val Gly Val Pro Gly Tyr Gly Val Pro Gly Lys Gly Val Pro Gly Val
            180                 185                 190 ggc gta ccg ggt tac ggc gta ccg ggt aaa ggg gtt cca ggc gtg ggt    624
Gly Val Pro Gly Tyr Gly Val Pro Gly Lys Gly Val Pro Gly Val Gly
        195                 200                 205 gta ccg ggc tat ggg gtg ccg ggt aaa ggc gtt ccg ggt gtg ggc gta    672
Val Pro Gly Tyr Gly Val Pro Gly Lys Gly Val Pro Gly Val Gly Val
    210                 215                 220 ccg ggt tac ggc gta ccg ggt aaa ggg gtt cca ggc gtg ggt gta ccg    720
Pro Gly Tyr Gly Val Pro Gly Lys Gly Val Pro Gly Val Gly Val Pro
225                 230                 235                 240
```

| | |
|---|---|
| ggc tat ggg gtg ccg ggt aaa ggc gtt ccg ggt gtg ggc gta ccg ggt<br>Gly Tyr Gly Val Pro Gly Lys Gly Val Pro Gly Val Gly Val Pro Gly<br>245 250 255 | 768 |
| tac ggc gta ccg ggt aaa ggg gtt cca ggc gtg ggt gta ccg ggc tat<br>Tyr Gly Val Pro Gly Lys Gly Val Pro Gly Val Gly Val Pro Gly Tyr<br>260 265 270 | 816 |
| ggg gtg ccg ggt aaa ggc gtt ccg ggt gtg gcc gta ccg ggt tac ggc<br>Gly Val Pro Gly Lys Gly Val Pro Gly Val Gly Val Pro Gly Tyr Gly<br>275 280 285 | 864 |
| gta ccg ggt aaa ggg gtt cca ggc gtg ggt gta ccg ggc tat ggg gtg<br>Val Pro Gly Lys Gly Val Pro Gly Val Gly Val Pro Gly Tyr Gly Val<br>290 295 300 | 912 |
| ccg ggt aaa ggc gtt ccg ggt gtg ggc gta ccg ggt tac ggc gta ccg<br>Pro Gly Lys Gly Val Pro Gly Val Gly Val Pro Gly Tyr Gly Val Pro<br>305 310 315 320 | 960 |
| ggt aaa ggg gtt cca ggc gtg ggt gta ccg ggc tat ggg gtg ccg ggt<br>Gly Lys Gly Val Pro Gly Val Gly Val Pro Gly Tyr Gly Val Pro Gly<br>325 330 335 | 1008 |
| aaa ggc gtt ccg ggt gtg ggc gta ccg ggt tac ggc gta ccg ggt aaa<br>Lys Gly Val Pro Gly Val Gly Val Pro Gly Tyr Gly Val Pro Gly Lys<br>340 345 350 | 1056 |
| ggg gtt cca ggc gtg ggt gta ccg ggc tat ggg gtg ccg ggt aaa ggc<br>Gly Val Pro Gly Val Gly Val Pro Gly Tyr Gly Val Pro Gly Lys Gly<br>355 360 365 | 1104 |
| gtt ccg ggt gtg ggc gta ccg ggt tac ggc gta ccg ggt aaa ggg gtt<br>Val Pro Gly Val Gly Val Pro Gly Tyr Gly Val Pro Gly Lys Gly Val<br>370 375 380 | 1152 |
| cca ggc gtg ggt gta ccg ggc tat ggg gtg ccg ggt aaa ggc gtt ccg<br>Pro Gly Val Gly Val Pro Gly Tyr Gly Val Pro Gly Lys Gly Val Pro<br>385 390 395 400 | 1200 |
| ggt gtg ggc gta ccg ggt tac ggc gta ccg ggt aaa ggg gtt cca ggc<br>Gly Val Gly Val Pro Gly Tyr Gly Val Pro Gly Lys Gly Val Pro Gly<br>405 410 415 | 1248 |
| gtg ggt gta ccg ggc tat ggg gtg ccg ggt aaa ggc gtt ccg ggt gtg<br>Val Gly Val Pro Gly Tyr Gly Val Pro Gly Lys Gly Val Pro Gly Val<br>420 425 430 | 1296 |
| ggc gta ccg ggt tac ggc gta ccg ggt aaa ggg gtt cca ggc gtg ggt<br>Gly Val Pro Gly Tyr Gly Val Pro Gly Lys Gly Val Pro Gly Val Gly<br>435 440 445 | 1344 |
| gta ccg ggc tat ggg gtg ccg ggt aaa ggc gtt ccg ggt gtg ggc gta<br>Val Pro Gly Tyr Gly Val Pro Gly Lys Gly Val Pro Gly Val Gly Val<br>450 455 460 | 1392 |
| ccg ggt tac ggc gta ccg ggt aaa ggg gtt cca ggc gtg ggt gta ccg<br>Pro Gly Tyr Gly Val Pro Gly Lys Gly Val Pro Gly Val Gly Val Pro<br>465 470 475 480 | 1440 |
| ggc tat ggg gtg ccg ggt aaa ggc gtt ccg ggt gtg ggc gta ccg ggt<br>Gly Tyr Gly Val Pro Gly Lys Gly Val Pro Gly Val Gly Val Pro Gly<br>485 490 495 | 1488 |
| tac ggc gta ccg ggt aaa ggg gtt cca ggc gtg ggt gta ccg gta gcg<br>Tyr Gly Val Pro Gly Lys Gly Val Pro Gly Val Gly Val Pro Val Ala<br>500 505 510 | 1536 |
| gac cgt gga atg cgg ctc gag<br>Asp Arg Gly Met Arg Leu Glu<br>515 | 1557 |

<210> SEQ ID NO 6
<211> LENGTH: 519
<212> TYPE: PRT
<213> ORGANISM: Artificial Sequence
<220> FEATURE:
<223> OTHER INFORMATION: Synthetic Construct

<400> SEQUENCE: 6

```
Met Met Ala Ser Met Thr Gly Gly Gln Gln Met Gly His His His His
1               5                   10                  15
His His His Asp Asp Asp Asp Lys Leu Asp Gly Thr Leu Pro Gly Tyr
                20                  25                  30
Gly Val Pro Gly Lys Gly Val Pro Gly Val Gly Val Pro Gly Tyr Gly
            35                  40                  45
Val Pro Gly Lys Gly Val Pro Gly Val Gly Val Pro Gly Tyr Gly Val
        50                  55                  60
Pro Gly Lys Gly Val Pro Gly Val Gly Val Pro Gly Tyr Gly Val Pro
65                  70                  75                  80
Gly Lys Gly Val Pro Gly Val Gly Val Pro Gly Tyr Gly Val Pro Gly
                85                  90                  95
Lys Gly Val Pro Gly Val Gly Val Pro Gly Tyr Gly Val Pro Gly Lys
            100                 105                 110
Gly Val Pro Gly Val Gly Val Pro Gly Tyr Gly Val Pro Gly Lys Gly
        115                 120                 125
Val Pro Gly Val Gly Val Pro Gly Tyr Gly Val Pro Gly Lys Gly Val
    130                 135                 140
Pro Gly Val Gly Val Pro Gly Tyr Gly Val Pro Gly Lys Gly Val Pro
145                 150                 155                 160
Gly Val Gly Val Pro Gly Tyr Gly Val Pro Gly Lys Gly Val Pro Gly
                165                 170                 175
Val Gly Val Pro Gly Tyr Gly Val Pro Gly Lys Gly Val Pro Gly Val
            180                 185                 190
Gly Val Pro Gly Tyr Gly Val Pro Gly Lys Gly Val Pro Gly Val Gly
        195                 200                 205
Val Pro Gly Tyr Gly Val Pro Gly Lys Gly Val Pro Gly Val Gly Val
    210                 215                 220
Pro Gly Tyr Gly Val Pro Gly Lys Gly Val Pro Gly Val Gly Val Pro
225                 230                 235                 240
Gly Tyr Gly Val Pro Gly Lys Gly Val Pro Gly Val Gly Val Pro Gly
                245                 250                 255
Tyr Gly Val Pro Gly Lys Gly Val Pro Gly Val Gly Val Pro Gly Tyr
            260                 265                 270
Gly Val Pro Gly Lys Gly Val Pro Gly Val Gly Val Pro Gly Tyr Gly
        275                 280                 285
Val Pro Gly Lys Gly Val Pro Gly Val Gly Val Pro Gly Tyr Gly Val
    290                 295                 300
Pro Gly Lys Gly Val Pro Gly Val Gly Val Pro Gly Tyr Gly Val Pro
305                 310                 315                 320
Gly Lys Gly Val Pro Gly Val Gly Val Pro Gly Tyr Gly Val Pro Gly
                325                 330                 335
Lys Gly Val Pro Gly Val Gly Val Pro Gly Tyr Gly Val Pro Gly Lys
            340                 345                 350
Gly Val Pro Gly Val Gly Val Pro Gly Tyr Gly Val Pro Gly Lys Gly
        355                 360                 365
Val Pro Gly Val Gly Val Pro Gly Tyr Gly Val Pro Gly Lys Gly Val
    370                 375                 380
Pro Gly Val Gly Val Pro Gly Tyr Gly Val Pro Gly Lys Gly Val Pro
385                 390                 395                 400
Gly Val Gly Val Pro Gly Tyr Gly Val Pro Gly Lys Gly Val Pro Gly
```

```
                405                 410                 415
Val Gly Val Pro Gly Tyr Gly Val Pro Gly Lys Gly Val Pro Gly Val
            420                 425                 430

Gly Val Pro Gly Tyr Gly Val Pro Gly Lys Gly Val Pro Gly Val Gly
            435                 440                 445

Val Pro Gly Tyr Gly Val Pro Gly Lys Gly Val Pro Gly Val Gly Val
    450                 455                 460

Pro Gly Tyr Gly Val Pro Gly Lys Gly Val Pro Gly Val Gly Val Pro
465                 470                 475                 480

Gly Tyr Gly Val Pro Gly Lys Gly Val Pro Gly Val Gly Val Pro Gly
            485                 490                 495

Tyr Gly Val Pro Gly Lys Gly Val Pro Gly Val Gly Val Pro Val Ala
            500                 505                 510

Asp Arg Gly Met Arg Leu Glu
            515

<210> SEQ ID NO 7
<211> LENGTH: 798
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(798)

<400> SEQUENCE: 7 atg agc aaa ggt ccg ggt gtc gac ggg acc ctc ccg ggc tat ggg gtg         48
Met Ser Lys Gly Pro Gly Val Asp Gly Thr Leu Pro Gly Tyr Gly Val
1               5                   10                  15 ccg ggt aaa ggc gtt ccg ggt gtg ggc gta ccg ggt tac ggc gta ccg         96
Pro Gly Lys Gly Val Pro Gly Val Gly Val Pro Gly Tyr Gly Val Pro
                20                  25                  30 ggt aaa ggg gtt cca ggc gtg ggt gta ccg ggc tat ggg gtg ccg ggt        144
Gly Lys Gly Val Pro Gly Val Gly Val Pro Gly Tyr Gly Val Pro Gly
            35                  40                  45 aaa ggc gtt ccg ggt gtg ggc gta ccg ggt tac ggc gta ccg ggt aaa        192
Lys Gly Val Pro Gly Val Gly Val Pro Gly Tyr Gly Val Pro Gly Lys
        50                  55                  60 ggg gtt cca ggc gtg ggt gta ccg ggc tat ggg gtg ccg ggt aaa ggc        240
Gly Val Pro Gly Val Gly Val Pro Gly Tyr Gly Val Pro Gly Lys Gly
65                  70                  75                  80 gtt ccg ggt gtg ggc gta ccg ggt tac ggc gta ccg ggt aaa ggg gtt        288
Val Pro Gly Val Gly Val Pro Gly Tyr Gly Val Pro Gly Lys Gly Val
                85                  90                  95 cca ggc gtg ggt gta ccg ggc tat ggg gtg ccg ggt aaa ggc gtt ccg        336
Pro Gly Val Gly Val Pro Gly Tyr Gly Val Pro Gly Lys Gly Val Pro
            100                 105                 110 ggt gtg ggc gta ccg ggt tac ggc gta ccg ggt aaa ggg gtt cca ggc        384
Gly Val Gly Val Pro Gly Tyr Gly Val Pro Gly Lys Gly Val Pro Gly
        115                 120                 125 gtg ggt gta ccg ggc tat ggg gtg ccg ggt aaa ggc gtt ccg ggt gtg        432
Val Gly Val Pro Gly Tyr Gly Val Pro Gly Lys Gly Val Pro Gly Val
    130                 135                 140 ggc gta ccg ggt tac ggc gta ccg ggt aaa ggg gtt cca ggc gtg ggt        480
Gly Val Pro Gly Tyr Gly Val Pro Gly Lys Gly Val Pro Gly Val Gly
145                 150                 155                 160 gta ccg ggc tat ggg gtg ccg ggt aaa ggc gtt ccg ggt gtg ggc gta        528
Val Pro Gly Tyr Gly Val Pro Gly Lys Gly Val Pro Gly Val Gly Val
                165                 170                 175
```

```
                                                              -continued ccg ggt tac ggc gta ccg ggt aaa ggg gtt cca ggc gtg ggt gta ccg       576
Pro Gly Tyr Gly Val Pro Gly Lys Gly Val Pro Gly Val Gly Val Pro
            180                 185                 190 ggc tat ggg gtg ccg ggt aaa ggc gtt ccg ggt gtg ggc gta ccg ggt       624
Gly Tyr Gly Val Pro Gly Lys Gly Val Pro Gly Val Gly Val Pro Gly
        195                 200                 205 tac ggc gta ccg ggt aaa ggg gtt cca ggc gtg ggt gta ccg ggc tat       672
Tyr Gly Val Pro Gly Lys Gly Val Pro Gly Val Gly Val Pro Gly Tyr
    210                 215                 220 ggg gtg ccg ggt aaa ggc gtt ccg ggt gtg ggc gta ccg ggt tac ggc       720
Gly Val Pro Gly Lys Gly Val Pro Gly Val Gly Val Pro Gly Tyr Gly
225                 230                 235                 240 gta ccg ggt aaa ggg gtt cca ggc gtg ggt gta ccg gta gcg gac cgt       768
Val Pro Gly Lys Gly Val Pro Gly Val Gly Val Pro Val Ala Asp Arg
                245                 250                 255 gga atg cgg ctc gac aaa gaa ttc ctc gag                               798
Gly Met Arg Leu Asp Lys Glu Phe Leu Glu
                260                 265

<210> SEQ ID NO 8
<211> LENGTH: 266
<212> TYPE: PRT
<213> ORGANISM: Artificial Sequence
<220> FEATURE:
<223> OTHER INFORMATION: Synthetic Construct

<400> SEQUENCE: 8

Met Ser Lys Gly Pro Gly Val Asp Gly Thr Leu Pro Gly Tyr Gly Val
1               5                   10                  15

Pro Gly Lys Gly Val Pro Gly Val Gly Val Pro Gly Tyr Gly Val Pro
            20                  25                  30

Gly Lys Gly Val Pro Gly Val Gly Val Pro Gly Tyr Gly Val Pro Gly
        35                  40                  45

Lys Gly Val Pro Gly Val Gly Val Pro Gly Tyr Gly Val Pro Gly Lys
    50                  55                  60

Gly Val Pro Gly Val Gly Val Pro Gly Tyr Gly Val Pro Gly Lys Gly
65                  70                  75                  80

Val Pro Gly Val Gly Val Pro Gly Tyr Gly Val Pro Gly Lys Gly Val
                85                  90                  95

Pro Gly Val Gly Val Pro Gly Tyr Gly Val Pro Gly Lys Gly Val Pro
            100                 105                 110

Gly Val Gly Val Pro Gly Tyr Gly Val Pro Gly Lys Gly Val Pro Gly
        115                 120                 125

Val Gly Val Pro Gly Tyr Gly Val Pro Gly Lys Gly Val Pro Gly Val
    130                 135                 140

Gly Val Pro Gly Tyr Gly Val Pro Gly Lys Gly Val Pro Gly Val Gly
145                 150                 155                 160

Val Pro Gly Tyr Gly Val Pro Gly Lys Gly Val Pro Gly Val Gly Val
                165                 170                 175

Pro Gly Tyr Gly Val Pro Gly Lys Gly Val Pro Gly Val Gly Val Pro
            180                 185                 190

Gly Tyr Gly Val Pro Gly Lys Gly Val Pro Gly Val Gly Val Pro Gly
        195                 200                 205

Tyr Gly Val Pro Gly Lys Gly Val Pro Gly Val Gly Val Pro Gly Tyr
    210                 215                 220

Gly Val Pro Gly Lys Gly Val Pro Gly Val Gly Val Pro Gly Tyr Gly
225                 230                 235                 240
```

Val Pro Gly Lys Gly Val Pro Gly Val Gly Val Pro Val Ala Asp Arg
                245                 250                 255

Gly Met Arg Leu Asp Lys Glu Phe Leu Glu
            260                 265

<210> SEQ ID NO 9
<211> LENGTH: 1161
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1161)

<400> SEQUENCE: 9

| | | |
|---|---|---:|
| atg agc aaa ggt ccg ggt gtc gac ggg acc ctc ccg ggc tac ggt gtg<br>Met Ser Lys Gly Pro Gly Val Asp Gly Thr Leu Pro Gly Tyr Gly Val<br>1               5                   10                  15 | | 48 |
| ccg ggt aag ggc gtt ccg ggt gtg ggc gtt ccg ggt tgc ggc gtg ccg<br>Pro Gly Lys Gly Val Pro Gly Val Gly Val Pro Gly Cys Gly Val Pro<br>            20                  25                  30 | | 96 |
| ggt aaa ggc gtt ccg ggt gtg ggc gta ccg ggc tac ggt gtg ccg ggt<br>Gly Lys Gly Val Pro Gly Val Gly Val Pro Gly Tyr Gly Val Pro Gly<br>        35                  40                  45 | | 144 |
| aag ggc gtt ccg ggt gtg ggc gtt ccg ggt tgc ggc gtg ccg ggt aaa<br>Lys Gly Val Pro Gly Val Gly Val Pro Gly Cys Gly Val Pro Gly Lys<br>    50                  55                  60 | | 192 |
| ggc gtt ccg ggt gtg ggc gta ccg ggc tac ggt gtg ccg ggt aag ggc<br>Gly Val Pro Gly Val Gly Val Pro Gly Tyr Gly Val Pro Gly Lys Gly<br>65                  70                  75                  80 | | 240 |
| gtt ccg ggt gtg ggc gtt ccg ggt tgc ggc gtg ccg ggt aaa ggc gtt<br>Val Pro Gly Val Gly Val Pro Gly Cys Gly Val Pro Gly Lys Gly Val<br>                85                  90                  95 | | 288 |
| ccg ggt gtg ggc gta ccg ggc tac ggt gtg ccg ggt aag ggc gtt ccg<br>Pro Gly Val Gly Val Pro Gly Tyr Gly Val Pro Gly Lys Gly Val Pro<br>            100                 105                 110 | | 336 |
| ggt gtg ggc gtt ccg ggt tgc ggc gtg ccg ggt aaa ggc gtt ccg ggt<br>Gly Val Gly Val Pro Gly Cys Gly Val Pro Gly Lys Gly Val Pro Gly<br>        115                 120                 125 | | 384 |
| gtg ggc gta ccg ggc tac ggt gtg ccg ggt aag ggc gtt ccg ggt gtg<br>Val Gly Val Pro Gly Tyr Gly Val Pro Gly Lys Gly Val Pro Gly Val<br>    130                 135                 140 | | 432 |
| ggc gtt ccg ggt tgc ggc gtg ccg ggt aaa ggc gtt ccg ggt gtg ggc<br>Gly Val Pro Gly Cys Gly Val Pro Gly Lys Gly Val Pro Gly Val Gly<br>145                 150                 155                 160 | | 480 |
| gta ccg ggc tac ggt gtg ccg ggt aag ggc gtt ccg ggt gtg ggc gtt<br>Val Pro Gly Tyr Gly Val Pro Gly Lys Gly Val Pro Gly Val Gly Val<br>                165                 170                 175 | | 528 |
| ccg ggt tgc ggc gtg ccg ggt aaa ggc gtt ccg ggt gtg ggc gta ccg<br>Pro Gly Cys Gly Val Pro Gly Lys Gly Val Pro Gly Val Gly Val Pro<br>            180                 185                 190 | | 576 |
| ggc tac ggt gtg ccg ggt aag ggc gtt ccg ggt gtg ggc gtt ccg ggt<br>Gly Tyr Gly Val Pro Gly Lys Gly Val Pro Gly Val Gly Val Pro Gly<br>        195                 200                 205 | | 624 |
| tgc ggc gtg ccg ggt aaa ggc gtt ccg ggt gtg ggc gta ccg ggc tac<br>Cys Gly Val Pro Gly Lys Gly Val Pro Gly Val Gly Val Pro Gly Tyr<br>    210                 215                 220 | | 672 |
| ggt gtg ccg ggt aag ggc gtt ccg ggt gtg ggc gtt ccg ggt tgc ggc<br>Gly Val Pro Gly Lys Gly Val Pro Gly Val Gly Val Pro Gly Cys Gly<br>225                 230                 235                 240 | | 720 |

```
gtg ccg ggt aaa ggc gtt ccg ggt gtg ggc gta ccg ggc tac ggt gtg      768
Val Pro Gly Lys Gly Val Pro Gly Val Gly Val Pro Gly Tyr Gly Val
            245                 250                 255 ccg ggt aag ggc gtt ccg ggt gtg ggc gtt ccg ggt tgc ggc gtg ccg      816
Pro Gly Lys Gly Val Pro Gly Val Gly Val Pro Gly Cys Gly Val Pro
        260                 265                 270 ggt aaa ggc gtt ccg ggt gtg ggc gta ccg ggc tac ggt gtg ccg ggt      864
Gly Lys Gly Val Pro Gly Val Gly Val Pro Gly Tyr Gly Val Pro Gly
    275                 280                 285 aag ggc gtt ccg ggt gtg ggc gtt ccg ggt tgc ggc gtg ccg ggt aaa      912
Lys Gly Val Pro Gly Val Gly Val Pro Gly Cys Gly Val Pro Gly Lys
290                 295                 300 ggc gtt ccg ggt gtg ggc gta ccg ggc tac ggt gtg ccg ggt aag ggc      960
Gly Val Pro Gly Val Gly Val Pro Gly Tyr Gly Val Pro Gly Lys Gly
305                 310                 315                 320 gtt ccg ggt gtg ggc gtt ccg ggt tgc ggc gtg ccg ggt aaa ggc gtt     1008
Val Pro Gly Val Gly Val Pro Gly Cys Gly Val Pro Gly Lys Gly Val
            325                 330                 335 ccg ggt gtg ggc gta ccg ggc tac ggt gtg ccg ggt aag ggc gtt ccg     1056
Pro Gly Val Gly Val Pro Gly Tyr Gly Val Pro Gly Lys Gly Val Pro
        340                 345                 350 ggt gtg ggc gtt ccg ggt tgc ggc gtg ccg ggt aaa ggc gtt ccg ggt     1104
Gly Val Gly Val Pro Gly Cys Gly Val Pro Gly Lys Gly Val Pro Gly
    355                 360                 365 gtg ggc gta ccg gta gcg gac cgt gga atg cgg ctc gag cac cac cac     1152
Val Gly Val Pro Val Ala Asp Arg Gly Met Arg Leu Glu His His His
370                 375                 380 cac cac cac                                                         1161
His His His
385

<210> SEQ ID NO 10
<211> LENGTH: 387
<212> TYPE: PRT
<213> ORGANISM: Artificial Sequence
<220> FEATURE:
<223> OTHER INFORMATION: Synthetic Construct

<400> SEQUENCE: 10

Met Ser Lys Gly Pro Gly Val Asp Gly Thr Leu Pro Gly Tyr Gly Val
1               5                   10                  15

Pro Gly Lys Gly Val Pro Gly Val Gly Val Pro Gly Cys Gly Val Pro
            20                  25                  30

Gly Lys Gly Val Pro Gly Val Gly Val Pro Gly Tyr Gly Val Pro Gly
        35                  40                  45

Lys Gly Val Pro Gly Val Gly Val Pro Gly Cys Gly Val Pro Gly Lys
    50                  55                  60

Gly Val Pro Gly Val Gly Val Pro Gly Tyr Gly Val Pro Gly Lys Gly
65                  70                  75                  80

Val Pro Gly Val Gly Val Pro Gly Cys Gly Val Pro Gly Lys Gly Val
                85                  90                  95

Pro Gly Val Gly Val Pro Gly Tyr Gly Val Pro Gly Lys Gly Val Pro
            100                 105                 110

Gly Val Gly Val Pro Gly Cys Gly Val Pro Gly Lys Gly Val Pro Gly
        115                 120                 125

Val Gly Val Pro Gly Tyr Gly Val Pro Gly Lys Gly Val Pro Gly Val
    130                 135                 140

Gly Val Pro Gly Cys Gly Val Pro Gly Lys Gly Val Pro Gly Val Gly
```

-continued

```
            145                 150                 155                 160
Val Pro Gly Tyr Gly Val Pro Gly Lys Gly Val Pro Gly Val Gly Val
                165                 170                 175
Pro Gly Cys Gly Val Pro Gly Lys Gly Val Pro Gly Val Gly Val Pro
                180                 185                 190
Gly Tyr Gly Val Pro Gly Lys Gly Val Pro Gly Val Gly Val Pro Gly
                195                 200                 205
Cys Gly Val Pro Gly Lys Gly Val Pro Gly Val Gly Val Pro Gly Tyr
        210                 215                 220
Gly Val Pro Gly Lys Gly Val Pro Gly Val Gly Val Pro Gly Cys Gly
225                 230                 235                 240
Val Pro Gly Lys Gly Val Pro Gly Val Gly Val Pro Gly Tyr Gly Val
                245                 250                 255
Pro Gly Lys Gly Val Pro Gly Val Gly Val Pro Gly Cys Gly Val Pro
                260                 265                 270
Gly Lys Gly Val Pro Gly Val Gly Val Pro Gly Tyr Gly Val Pro Gly
            275                 280                 285
Lys Gly Val Pro Gly Val Gly Val Pro Gly Cys Gly Val Pro Gly Lys
            290                 295                 300
Gly Val Pro Gly Val Gly Val Pro Gly Tyr Gly Val Pro Gly Lys Gly
305                 310                 315                 320
Val Pro Gly Val Gly Val Pro Gly Cys Gly Val Pro Gly Lys Gly Val
                325                 330                 335
Pro Gly Val Gly Val Pro Gly Tyr Gly Val Pro Gly Lys Gly Val Pro
                340                 345                 350
Gly Val Gly Val Pro Gly Cys Gly Val Pro Gly Lys Gly Val Pro Gly
            355                 360                 365
Val Gly Val Pro Val Ala Asp Arg Gly Met Arg Leu Glu His His His
        370                 375                 380
His His His
385

<210> SEQ ID NO 11
<211> LENGTH: 5
<212> TYPE: PRT
<213> ORGANISM: artificial sequence
<220> FEATURE:
<223> OTHER INFORMATION: ELP protein repeating units.  X is any amino
      acid except proline
<220> FEATURE:
<221> NAME/KEY: X
<222> LOCATION: (4)..(4)
<223> OTHER INFORMATION: X is any amino acid except proline

<400> SEQUENCE: 11

Val Pro Gly Xaa Gly
1               5

<210> SEQ ID NO 12
<211> LENGTH: 5
<212> TYPE: PRT
<213> ORGANISM: artificial sequence
<220> FEATURE:
<223> OTHER INFORMATION: HD-ELP [YKV-48] insert

<400> SEQUENCE: 12

Ser Lys Gly Pro Gly
1               5
```

-continued

```
<210> SEQ ID NO 13
<211> LENGTH: 5
<212> TYPE: PRT
<213> ORGANISM: artificial sequence
<220> FEATURE:
<223> OTHER INFORMATION: ELP protein repeating units, wherein X is Lys,
      Tyr, or Cys
<220> FEATURE:
<221> NAME/KEY: X
<222> LOCATION: (4)..(4)
<223> OTHER INFORMATION: X is lysine, tyrosine or cysteine

<400> SEQUENCE: 13

Val Pro Gly Xaa Gly
1               5

<210> SEQ ID NO 14
<211> LENGTH: 279
<212> TYPE: PRT
<213> ORGANISM: artificial sequence
<220> FEATURE:
<223> OTHER INFORMATION: acEL-[YKV-48], also known as acEL(YKV)16

<400> SEQUENCE: 14

Met Met Ala Ser Met Thr Gly Gly Gln Gln Met Gly His His His His
1               5                   10                  15

His His His Asp Asp Asp Asp Lys Leu Asp Gly Thr Leu Pro Gly Tyr
                20                  25                  30

Gly Val Pro Gly Lys Gly Val Pro Gly Val Gly Val Pro Gly Tyr Gly
            35                  40                  45

Val Pro Gly Lys Gly Val Pro Gly Val Gly Val Pro Gly Tyr Gly Val
        50                  55                  60

Pro Gly Lys Gly Val Pro Gly Val Gly Val Pro Gly Tyr Gly Val Pro
65                  70                  75                  80

Gly Lys Gly Val Pro Gly Val Gly Val Pro Gly Tyr Gly Val Pro Gly
                85                  90                  95

Lys Gly Val Pro Gly Val Gly Val Pro Gly Tyr Gly Val Pro Gly Lys
            100                 105                 110

Gly Val Pro Gly Val Gly Val Pro Gly Tyr Gly Val Pro Gly Lys Gly
        115                 120                 125

Val Pro Gly Val Gly Val Pro Gly Tyr Gly Val Pro Gly Lys Gly Val
    130                 135                 140

Pro Gly Val Gly Val Pro Gly Tyr Gly Val Pro Gly Lys Gly Val Pro
145                 150                 155                 160

Gly Val Gly Val Pro Gly Tyr Gly Val Pro Gly Lys Gly Val Pro Gly
                165                 170                 175

Val Gly Val Pro Gly Tyr Gly Val Pro Gly Lys Gly Val Pro Gly Val
            180                 185                 190

Gly Val Pro Gly Tyr Gly Val Pro Gly Lys Gly Val Pro Gly Val Gly
        195                 200                 205

Val Pro Gly Tyr Gly Val Pro Gly Lys Gly Val Pro Gly Val Gly Val
    210                 215                 220

Pro Gly Tyr Gly Val Pro Gly Lys Gly Val Pro Gly Val Gly Val Pro
225                 230                 235                 240

Gly Tyr Gly Val Pro Gly Lys Gly Val Pro Gly Val Gly Val Pro Gly
                245                 250                 255
```

```
Tyr Gly Val Pro Gly Lys Gly Val Pro Gly Val Gly Val Pro Val Ala
            260                 265                 270

Asp Arg Gly Met Arg Leu Glu
            275
```